United States Patent
Hargis et al.

(10) Patent No.: US 12,377,122 B2
(45) Date of Patent: Aug. 5, 2025

(54) ***BACILLUS* ISOLATE COMPOSITIONS AND METHODS OF USING AND PRODUCING THE SAME**

(71) Applicant: THE BOARD OF TRUSTEES OF THE UNIVERSITY OF ARKANSAS, Little Rock, AR (US)

(72) Inventors: Billy M. Hargis, Fayetteville, AR (US); Lucas Elzie Graham, Fayetteville, AR (US); Kyle Dean Teague, Siloam Springs, AR (US); Juan David Latorre, Fayetteville, AR (US); Samuel J. Rochell, Fayetteville, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 597 days.

(21) Appl. No.: 17/621,512

(22) PCT Filed: Jun. 22, 2020

(86) PCT No.: PCT/US2020/038954
§ 371 (c)(1),
(2) Date: Dec. 21, 2021

(87) PCT Pub. No.: WO2020/257769
PCT Pub. Date: Dec. 24, 2020

(65) Prior Publication Data
US 2022/0347234 A1 Nov. 3, 2022

Related U.S. Application Data

(60) Provisional application No. 62/865,010, filed on Jun. 21, 2019.

(51) Int. Cl.
*A61K 35/742* (2015.01)
*A23L 33/135* (2016.01)
*C12N 1/20* (2006.01)
*C12R 1/07* (2006.01)

(52) U.S. Cl.
CPC .......... *A61K 35/742* (2013.01); *A23L 33/135* (2016.08); *C12N 1/205* (2021.05); *C12R 2001/07* (2021.05)

(58) Field of Classification Search
None
See application file for complete search history.

(56) References Cited

U.S. PATENT DOCUMENTS

| | | | |
|---|---|---|---|
| 8,975,056 | B2 | 3/2015 | Cascao-Pereira et al. |
| 9,005,601 | B2 | 4/2015 | Hargis et al. |
| 9,040,278 | B2 | 5/2015 | Cascao-Pereira et al. |
| 9,040,279 | B2 | 5/2015 | Breneman et al. |
| 10,959,447 | B2 | 3/2021 | Hargis et al. |
| 2008/0050779 | A1 | 2/2008 | Defachelles et al. |
| 2008/0057047 | A1 | 3/2008 | Sas et al. |
| 2011/0021461 | A1 | 1/2011 | Vazquez-Anon et al. |
| 2017/0096657 | A1 | 4/2017 | Gosselin et al. |
| 2017/0340682 | A1* | 11/2017 | Rehberger ............. A23K 10/18 |
| 2018/0206525 | A1 | 7/2018 | Hargis et al. |

FOREIGN PATENT DOCUMENTS

| | | |
|---|---|---|
| WO | 2004080200 A1 | 9/2004 |
| WO | 2016046155 A1 | 3/2016 |

OTHER PUBLICATIONS

Menconi, A., et al. "Physiological properties and Salmonella growth inhibition of probiotic Bacillus strains isolated from environmental and poultry sources." International journal of bacteriology 2013 (2013).
Monisha, R., et al. (2009). Partial purification and characterization of Bacillus pumilus xylanase from soil source. KUSET, 5, 137-148.
Mukherjee et al., Role of Fermentation in Improving Nutritional Quality of Soybean Meal—A Review, Asian Australas. J. Anim. Sci. (2016) 29(11):1523-1529.
Murphy, T. C., et al. "Broiler performance and in vivo viscosity as influenced by a range of xylanases, varying in ability to effect wheat in vitro viscosity." British Poultry Science 50.6 (2009): 716-724.
Sen, S., et al. (2012). Effect of supplementation of Bacillus subtilis LS 1-2 to broiler diets on growth performance, nutrient retention, caecal microbiology and small intestinal morphology. Res. Vet. Sci. 93, 264-268.
Shirzadi, H. et al. "Influence of non starch polysaccharide-degrading enzymes on the meat yield and viscosity of jejunal digesta in broilers fed wheat/barley-based diet." African Journal of Biotechnology 9.10 (2010): 1517-1522.
Shivaramaiah, S., et al. "Evaluation of *Bacillus* species as potential candidates for direct-fed microbials in commercial poultry." Poultry Science 90.7 (2011): 1574-1580.
Slominski, B. A. "Recent advances in research on enzymes for poultry diets." Poultry Science 90.9 (2011): 2013-2023.
Tellez, G., et al. (2012). Probiotics/direct : fed microbials for Salmonella control in poultry. Food Res. Int. 45, 628-633.
Tellez, G., et al. (2013). Probiotics for human and poultry use in the control of gastrointestinal disease: a review of real-world experiences. Altern. Integ. Med. 2, 118. doi: 10.4172/2327-5162.1000118.
Tellez, G., et al. 2015. Role of a candidate Bacillus subtilis direct-fed microbial on digesta viscosity, bacterial translocation and bone mineralization in neonatal poults fed with a rye-based diet. International Poultry Scientific Forum in conjunction with the International Poultry Expo, Atlanta. Georgia.
Tellez. G., et al. Jan. 2014. Screening of bacteriocins like compounds synthesis from *Bacillus* sp. and the relation between diet composition, viscosity and proliferation of Clostridium perfringens using an in vitro digestive model. International Poultry Scientific Forum in conjunction with the International Poultry Expo, Atlanta. Georgia.

(Continued)

*Primary Examiner* — Jyoti Chawla
(74) *Attorney, Agent, or Firm* — Quarles & Brady, LLP

(57) ABSTRACT

The present invention provides *Bacillus* isolates, as well as probiotic and animal feed compositions comprising said isolates, which may be included in the diet of poultry to improve growth performance with reduced energy diets. Methods of using these compositions to improve nutritional uptake or to reduce the incidence of footpad dermatitis in poultry are also provided.

15 Claims, 17 Drawing Sheets

(56) References Cited

OTHER PUBLICATIONS

Wang, Z. R., et al. "Effects of enzyme supplementation on performance, nutrient digestibility, gastrointestinal morphology, and volatile fatty acid profiles in the hindgut of broilers fed wheat-based diets." Poultry Science 84.6 (2005): 875-881.
Wealleans et al., (2017) Performance, gut morphology and microbiology effects of a Bacillus probiotic, avilamycin and their combination in mixed grain boiler diets, British Poultry Science, 58:5, 523-529.
Wolfenden, R. E., et al. "Evaluation of selected direct-fed microbial candidates on live performance and *Salmonella* reduction in commercial turkey brooding houses." Poultry Science 90.11 (2011): 2627-2631.
Xu, X., et al. "Immunomodulatory effects of Bacillus subtilis (natto) B4 spores on murine macrophages." Microbiology and Immunology 56.12 (2012): 817-824.
Zou, J, et al. "Effects of exogenous enzymes and dietary energy on performance and digestive physiology of broilers." Journal of Animal Science and Biotechnology 4.1 (2013): 14.
Graham et al., Isolation and selection of *Bacillus* spp. as candidate directed microbials based on qualitative in vitro enzymatic hydrolysis of indigestible non-starch polysaccharides and oligosaccharides found in soybean meal [abstract]. In: 2020 International Poultry Scientific Forum; Jan. 27-28, 2020; Atlanta, Georgia. Abstract No. M82.
Teague et al., In vivo evaluation of Bacillus isolates selected based on qualitative in vitro enzyme activity against soybean meal carbohydrates as directed microbial candidates for broiler chickens [abstract]. In: 2020 International Poultry Scientific Forum; Jan. 27-28, 2020; Atlanta, Georgia. Abstract No. M83.
Restriction Requirement for U.S. Appl. No. 15/744,932 dated Jun. 27, 2019 (6 pages).
Office Action for U.S. Appl. No. 15/744,932 dated Dec. 12, 2019 (10 pages).
Adeola, O., et al. "Board-invited review: opportunities and challenges in using exogenous enzymes to improve nonruminant animal production." Journal of animal science 89.10 (2011): 3189-3218.
Ahmed, S. T., et al. "Effects of Bacillus amyloliquefaciens as a probiotic strain on growth performance, cecal microflora, and fecal noxious gas emissions of broiler chickens." Poultry Science 93.8 (2014): 1963-1971.
Alvarez-Olmos, M.I., et al. (2001). Probiotic agents and infectious diseases: a modern perspective on a traditional therapy. Clin. Infect. Dis. 32, 1567-1576.
Annett, C.B., et al. (2002). Necrotic enteritis: effect of barley, wheat and corn diets on proliferation of Clostridium perfringens type A. Avian Pathol. 31, 598-601.
Knudsen, K. E. B. (1997). Carbohydrate and lignin contents of plant materials used in animal feeding. Anim. Feed Sci. Technol. 67, 319-338.
Barbosa, T. M., et al. "Screening for Bacillus isolates in the broiler gastrointestinal tract." Appl. Environ. Microbiol. 71.2 (2005): 968-978.
Bedford, M.R., et al. (1991). The effect of pelleting, salt, and pentosanase on the viscosity of intestinal contents and the performance of broilers fed rye. Poult. Sci. 70, 1571-1577.
Bedford, M.R., et al. (1993). An in vitro assay for prediction of broiler intestinal viscosity and growth when fed rye-based diets in the presence of exogenous enzymes. Poult. Sci. 72, 137-143.
Bedford, M.R., et al. (1998). Exogenous enzymes for pigs and poultry. Nutr. Res. Rev. 11, 91-114. doi: 10.1079/NRR19980007.
Castanon, J.I. (2007). History of the use of antibiotic as growth promoters in European poultry feeds. Poult. Sci. 86, 2466-2471.
Chernick et al., (1948) A dietary factor regulating the enzyme content of the pancreas: Changes induced in size and proteolytic activity of the chick pancreas by the ingestion of raw soybean meal. Am. J. Physiol. 155:33-41.

Choct, M., et al. (1995). Nonstarch polysaccharide-degrading enzymes increase the performance of broiler chickens fed wheat of low apparent metabolizable energy. J. Nutr. 125, 485-492.
Choct, M., et al. (1996). Increased small intestinal fermentation is partly responsible for the anti-nutritive activity of non-starch polysaccharides in chickens. Br. Poult. Sci. 37, 609-621.
Cobb-Vantress, Inc. (2013). Cobb 500 broiler performance and nutrition supplement, accessed May 7, 2015, http://www.cobb-vantress.com/products/guidelibrary/cobbsasso/broiler-performance-and-nutrition-supplement.
Coon et al., (1990) Effect of oligosaccharide-free soybean meal on true metabolizable energy and fiber digetion in adult roosters. Poult. Sci. 69: 787-793.
Feng et al., Effects of Aspergillus oryzae 3.042 fermented soybean meal on growth performance and plasma biochemical parameters in broilers, Anim. Feed Sci Tech (2007) 134:235-242.
Flores, C., et al. Direct-fed microbial and its combination with xylanase, amylase, and protease enzymes in comparison with AGPs on broiler growth performance and foot-pad lesion development, The Journal of Applied Poultry Research, vol. 25, Issue 3, Sep. 1, 2016, pp. 328-337.
Friesen, O. D., et al. "The effect of enzyme supplementation on the apparent metabolizable energy and nutrient digestibilities of wheat, barley, oats, and rye for the young broiler chick." Poultry Science 71.10 (1992): 1710-1721.
Cartman, S.T., et al. (2008). Bacillus subtilis spores germinate in the chicken gastrointestinal tract. Appl. Environ. Microbial. 7 4, 5254-5258.
Gonzalez-Pastor, J.E., et al. (2003). Cannibalism by sporulating bacteria. Science 301, 510-513.
Graham et al. (2002) The effect of enzyme treatment of soybean meal on oligosaccharide disappearance and chick growth performance. Poult. Sci. 81:1014-1019.
Hirabayashi et al., Fermentation of soybean meal with Aspergillus usamii reduces phosphorus excretion in chicks, Poult Sci (1998) 77(4):552-6.
Hoa, T.T., et al. (2001). Fate and dissemination of Bacillus subtilis spores in a murine model. Appl. Environ. Microbial. 67, 3819-3823.
Hong, H.A., et al. (2005). The use of bacterial spore formers as, probiotics. FEMS Microbial. Rev. 29, 813-835.
Hong, H.A., et al. (2009). Bacillus subtilis isolated from the human gastrointestinal tract. Res. Microbial. 160, , 134-143. doi: 10.1016/j.resmic.2008.11.002.
Huang, J.M., et al. (2010). "Mucosal delivery of antigens using adsorption to bacterial spores." Vaccine 28.4 (2010): 1021-1030.
International Searching Authority, International Search Report and Written Opinion for application PCT/US2016/041977, mailed on Nov. 14, 2016.
International Searching Authority, International Search Report and Written Opinion for application PCT/US2020/038954, mailed on Oct. 2, 2020.
Jadamus, A. et al. "Growth behaviour of a spore forming probiotic strain in the gastrointestinal tract of broiler chicken and piglets." Archives of Animal Nutrition 54.1 (2001): 1-17.
Kiarie, E., et al. (2013). The role of added feed enzymes in promoting gut health in swine and poultry. Nutr. Res. Rev. 26, 71-88. doi: 10.1017/S0954422413000048.
Kocher et al. (2002) Effects of feed enzymes on nutritive value of soyabean meal fed to broilers. British Poultry Science 43: 54-63.
La Ragione, R.M., et al. (2003). "Competitive exclusion by Bacillus subtilis spores of *Salmonella enterica* serotype Enteritidis and Clostridium perfringens in young chickens." Veterinary microbiology 94.3: 245-256.
Latorre et al., Effects of the inclusion of a Bacillus direct-fed microbial on performance parameters, bone quality, recovered gut microflora, and intestinal morphology in broilers consuming a grower diet containing corn distillers dried grains with solubles, Poultry Science, vol. 95, Issue 8, Aug. 1, 2017, pp. 2728-2735.
Latorre et al. 2013. In Vitro enzyme production and viscosity determination by selective *Bacillus* spp. in different poultry diets. Symposium on gut health in production of food animals. Kansas City, MO.

(56) References Cited

OTHER PUBLICATIONS

Latorre et al. Jul. 14, 2014. Improvement of the nutritive value of rye for neonatal broiler chickens by Direct-fed microbial-induced bacterial translocation and viscosity reduction. Poultry Science Association Annual Meeting. Corpus Christi, Texas.
Latorre et al. Nov. 2014. The role of a selected Bacillus subtilis direct-fed microbial candidate on performance, intestinal viscosity, bacterial translocation and bone mineralization in broiler chickens consuming high NSP diets. Symposium on gut health in production of food animals. St. Louis Missouri.
Latorre, J. D., et al. "Evaluation and selection of *Bacillus* species based on enzyme production, antimicrobial activity, and biofilm synthesis as direct-fed microbial candidates for poultry." Frontiers in veterinary science 3 (2016): 95.
Latorre, J. D., et al. "Evaluation of germination, distribution, and persistence of Bacillus subtilis spores through the gastrointestinal tract of chickens." Poultry science 93.7 (2014): 1793-1800.
Latorre, J. D., et al. "Selection of *Bacillus* spp. for cellulase and xylanase production as direct-fed microbials to reduce digesta viscosity and Clostridium perfringens proliferation using an in vitro digestive model in different poultry diets." Frontiers in veterinary science 2 (2015): 25.
Latorre, J.D., et al. 2014. Role of a Bacillus subtilis direct-fed microbial on digesta viscosity, bacterial translocation and bone mineralization in neonatal poults fed with a rye-based diet. Front. Vet. Sci. 1 :26.
Latorre, J.D., X. Hernandez-Velasco, L. R. Bielke, J. L. Vicente, R. Wolfenden, A. Menconi, B. M. Hargis, and G. Tellez. 2015. Evaluation of a Bacillus subtilis direct-fed microbial on digesta viscosity, bacterial translocation, microbiota composition and bone mineralization in broiler chickens fed with a rye-based diet, Br Poult Sci 56 (6):723-32.
Layton, S.L., et al. (2013). The effect of a Lactobacillus-based probiotic for the control of necrotic enteritis in broilers. Food Nut. Sci. 4, 1-7.
Lei, X., et al. "Effect of Bacillus amyloliquefaciens-based direct-fed microbial on performance, nutrient utilization, intestinal morphology and cecal microflora in broiler chickens." Asian-Australasian Journal of Animal Sciences 28.2 (2015): 239.
Leser, T.D., et al. (2008). Germination and outgrowth of Bacillus subtilis and Bacillus licheniformis spores in the gastrointestinal tract of pigs. J. Appl. Microbial. 104, 1025-1033.
Li, Y., et al. "Bacillus amyloliquefaciens supplementation alleviates immunological stress in lipopolysaccharide-challenged broilers at early age." Poultry science 94.7 (2015): 1504-1511.
Loeffler, T. (2012) The effects of trypsin inhibitors on the nutritional value of various soy products and broiler performance.
Lopez, D., et al. "Cannibalism enhances biofilm development in Bacillus subtilis." Molecular microbiology 74.3 (2009):609-618.
Mahmood, K., et al. "Non-antibiotic strategies for the control of necrotic enteritis in poultry." World's Poultry Science Journal 70.4 (2014): 865-879.
Mathivanan et al., Feeding of Fermented Soybean Meal on Broiler Performance, Int. J. Poult. Sci. (2006) 5 (9):868-872.
McReynolds, J. L., et al. "Evaluation of immunosuppressants and dietary mechanisms in an experimental disease model for necrotic enteritis." Poultry science 83.12 (2004): 1948-1952.

* cited by examiner

BACILLUS ISOLATE COMPOSITIONS AND METHODS OF USING AND PRODUCING THE SAME

CROSS-REFERENCE TO RELATED APPLICATIONS

This patent application is a national stage filing under 35 U.S.C. § 371 of International Patent Application No. PCT/US2020/038954, filed Jun. 22, 2020, which claims the benefit of priority of U.S. Provisional Patent Application No. 62/865,010, filed Jun. 21, 2019, both of which are incorporated herein by reference in their entirety.

INTRODUCTION

Feed ingredients used for nutrition of monogastric animals contain anti-nutritional factors that are not only undigestible, but also deleterious to gut health within the animal. The non-starch polysaccharides (NSP) and oligosaccharides present mainly in soybean meal can lead to gut inflammation which results in poor nutrient absorption and bacterial leakage across the mucosal epithelium. The α-galactosides, raffinose and stachyose, are the primary oligosaccharides and make up 5-7% of soybean meal. They are considered anti-nutritional factors because they are poorly digestible and reduce the metabolizable energy (ME) and carbohydrate digestion of the meal. They can also cause wet feces, which can impact litter and air quality in poultry. This problem can be alleviated with the use of α-galactosidase enzymes to pretreat the soybean meal before feeding or by feeding these enzymes directly to the animal. This also reduces the quantity of soybean meal and energy dense feed ingredients (e.g., supplemental lipids) needed due to greater nutritional value and the increased concentration of digestible amino acids.

Recently, numerous biosynthetic enzymes have been marketed to break down non-digestible substrates in the feed. These products contain enzymes that can break down non-starch polysaccharides such as hemicellulose (hemicellulase) and arabinoxylans (xylanases), poorly digestible proteins (proteases), and others. In fact, almost all feed that is commercially produced for pigs and chickens contains exogenous phytase, an enzyme that breaks down phytate to release poorly available phosphorus from plant-based feedstuffs. These feed-grade enzymes have been widely adopted and their use depends on cost, availability, and feed ingredients (i.e., substrate). Enzymes are valuable for animal nutritionists as they allow for increased flexibility of feed ingredient selection based on least cost formulation. It is also thought that enzymes provide a nutritional "safety margin" in the event that the quality of preferred ingredients such as corn and soybean meal is less than anticipated due to agronomic or improper storage or processing conditions.

Although the addition of biosynthetic enzymes to animal feed has shown some success, the approach suffers from a number of shortcomings. First, the biosynthetic enzymes may not be stable and thus denature during heat treatments applied during feed processing. Enzyme stability is also a concern in the low pH environment of the animal gut leading to inefficient processing of anti-nutritional factors. Finally, the production and purification of biosynthetic enzymes can be costly leading to higher animal feed costs. Accordingly, there is a need in the art for new cost-effective feed supplements that increase nutrient uptake in animals and which retain stability both during feed processing and within the animal gut.

SUMMARY

In one aspect of the present invention, new isolates of *Bacillus* are provided. The *Bacillus* isolates may be in vegetative (i.e., cellular metabolic form) or spore form. A new *Bacillus* isolate designated as "Isolate 46" or "VWB46" is provided. The isolate has been deposited on Jun. 12, 2020 at the Agricultural Research Culture Collection (NRRL) under the terms of the Budapest treaty as Accession number NRRL B-67957. The isolate is a *Bacillus amyloliquefaciens*. A new *Bacillus* isolate designated as "Isolate 40" or "VWB40" is provided. The isolate has been deposited on Jun. 12, 2020 at the Agricultural Research Culture Collection (NRRL) under the terms of the Budapest Treaty as Accession Number NRRL B-67956. The isolate is also a *Bacillus amyloliquefaciens*.

In another aspect, the present invention relates to probiotic compositions. The probiotic compositions may include any one of or any combination of the *Bacillus* isolates described herein and a carrier. These compositions may be combined with other bacterial isolates in a probiotic composition.

In a further aspect of the present invention, animal feed compositions are provided. The animal feed compositions may include any of the *Bacillus* isolates or probiotic compositions described herein and a plant-based food source. Optionally, the animal feed compositions may additionally include a carbohydrate component, a protein component, a fat component, a mineral component, a vitamin component, or any combination thereof.

In a still further aspect, the present invention relates to methods for improving nutritional uptake in a subject. The methods may include administering to the subject an effective amount of any of the compositions (*Bacillus* isolates, probiotic compositions, or animal feed compositions) described herein.

In another aspect, the present invention relates to methods for producing an animal feed composition. The methods may include introducing any one of the *Bacillus* isolates or probiotic compositions described herein into the animal feed composition. Suitably, the feed composition is a dry mash or pelleted feed composition and the *Bacillus* isolate or probiotic composition is added prior to mixing the feed composition and the *Bacillus* isolates are added as spores.

DETAILED DESCRIPTION

Figure 1:
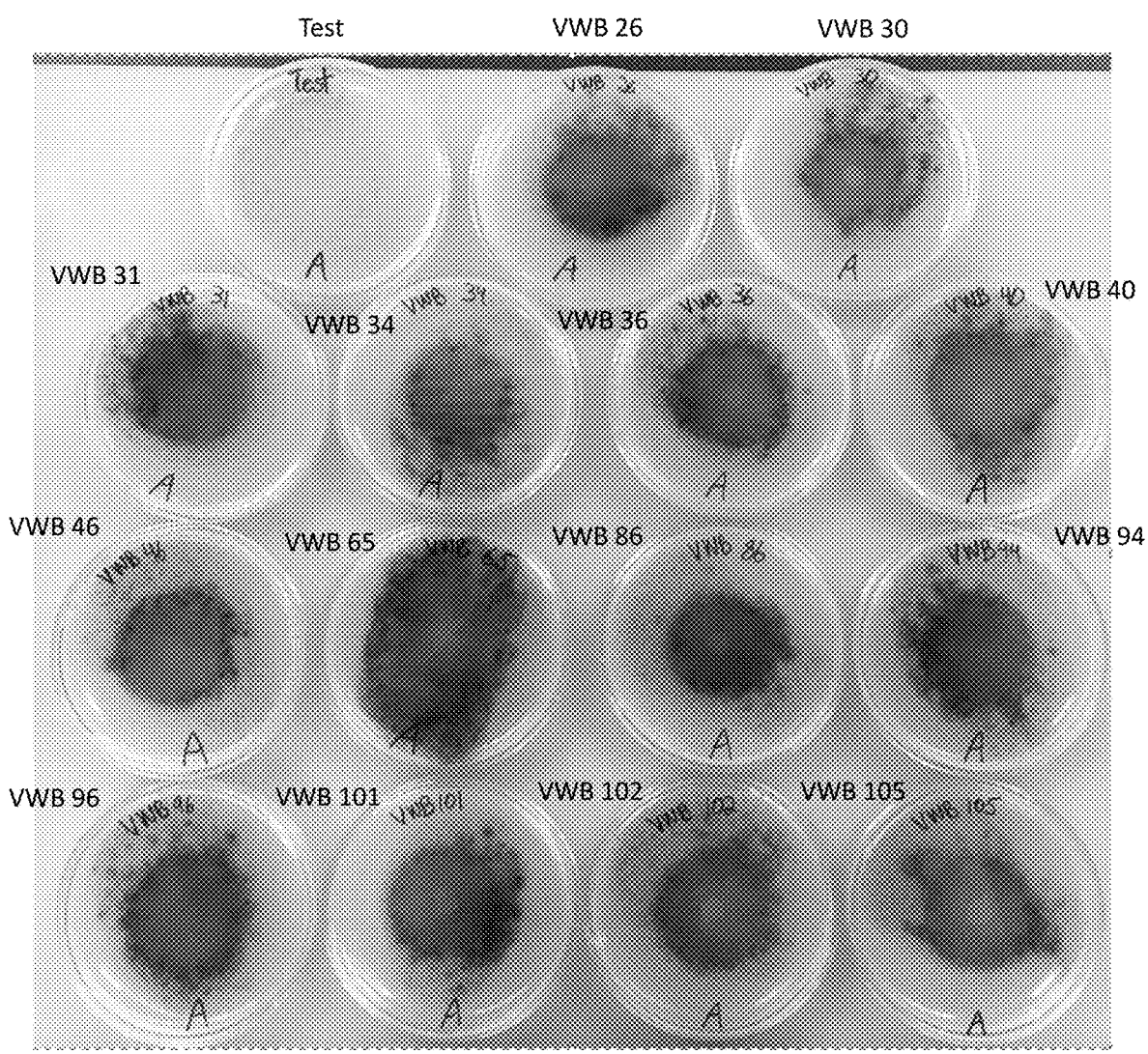
FIG. 1 shows isolate growth on ammonia media plates containing 0.0125% glucose with arabinoxylan soft agar overlays.

Here, in the non-limiting Examples, the present inventors have developed a serial screening method for the selection of specific spore-forming bacterial isolates (all of the genus *Bacillus*) for their ability to robustly form spores of high quality during appropriate incubation. The *Bacillus* isolate spores were selected to resist treatment with high temperatures, which are commonly applied during commercial feed production, and for their ability to produce enzymes capable of breaking down cellulose, xylans, mannans, and/or raffinose.

The present inventors further demonstrate, using multiple in vivo experiments in poultry, that dietary inclusion of spores from certain *Bacillus* isolates in chicken feed could improve poultry performance with reduced energy diets, including significant improvement in growth rate and feed efficiency of chickens when fed a low energy diet (LED). Additionally, inclusion of the spores in chicken feed improved carcass characteristics and lowered the incidence of footpad pododermatitis lesions. These results suggest the compositions described herein could be added to feed compositions to lower the cost of raising and caring for animals in meat production and allow the use of food-stuffs to make animal feed that would otherwise be considered too low in quality for such use. This may allow use of what may be considered waste products in animal feeds and could reduce the costs of production.

The present invention is superior to current exogenously produced, biosynthetic enzymes in several ways. First, due to the innate heat stability of *Bacillus*, the present isolates can be administered in both pelleted and non-pelleted feeds. Most enzyme supplements, on the other hand, are not stable at high temperatures and must be protectively coated or applied post pelleting. Application of products post pelleting however is not preferred, as it is often more expensive and obstructive to the feed milling process. The present *Bacillus* isolates are heat stable at normal feed milling temperatures and can be applied as a dry powder pre-pelleting.

Another advantage to our *Bacillus* isolates is that, unlike biosynthetic enzymes which are often produced in GMO (genetically modified organisms), the present isolates are natural producers of these enzymes and are simply selected without genetic modification. Thus, the isolates may help animal feed manufacturers address current consumer preference for non-GMO products.

Finally, biosynthetic enzymes are usually a single enzyme or a combination of a few enzymes. Although the activity of these enzymes is high for their specific substrate, if that substrate is not exposed due to the plant structure then it has no use. The plant packages nutrients in layers and without each specific enzyme to break down each layer, synthetic enzymes are not providing any benefits. The present *Bacillus* isolates, however, were selected to act on a multitude of substrates in a given feedstuff, not a single, specific substrate. Thus, when selected for the correct target(s), the present isolates produce the necessary enzymes to break down the packaged nutrients and release otherwise indigestible materials.

Compositions

*Bacillus* Isolates

In one aspect of the present invention, new isolates of *Bacillus* are provided. The *Bacillus* isolates may be in vegetative or spore form.

A new *Bacillus* isolate designated as "Isolate 46" is provided. The isolate has been deposited at the ARS Culture Collection (NRRL Accession No. B-67957).

A new *Bacillus* isolate designated as "Isolate 40" is provided. The isolate has been deposited at the ARS Culture Collection (NRRL Accession No. B-67956).

Probiotic Compositions

In another aspect, the present invention relates to probiotic compositions. The probiotic compositions may include any one of the *Bacillus* isolates described herein or a combination thereof and a carrier. Suitable carriers may include substances that aid in the formulation of a *Bacillus* isolate for administration to a subject. Carriers for water administration may include, without limitation, water; buffers such as phosphate, citrate, or other organic acids; or chelating agents such as EDTA. Carriers for feed administration in powdered form may include, without limitation, calcium carbonate, ground limestone, rice hulls, or other dry material to be added during mixing or on top of existing feed at the farm.

Animal Feed Compositions

In a further aspect of the present invention, animal feed compositions are provided. The animal feed compositions may include a plant-based food source. The animal feed compositions may include any of the *Bacillus* isolates or probiotic compositions described herein and a plant- or animal-based food source. Optionally, the animal feed compositions may also include a carbohydrate component, a protein component, a fat component, a mineral component, a vitamin component, or any combination thereof.

The animal feed compositions may include key nutrients needed to meet the dietary requirements of a particular subject. These key nutrients may include a protein component, a carbohydrate component, fats and oils, minerals, vitamins, or any combination thereof.

Common protein components found in animal feeds for example may include, without limitation, protein meals or protein derived from plant (vegetable or seed) and animal sources, such as soybean, oilseed, legumes, rice, abattoir, and fish processing by-products. Suitable plant-based food sources include the vegetable or fruit product and the seed, but also derivatives thereof. For example, soybean or other oilseed meal left over from oil or plant-based protein production, such as soybean meal, oilseed meal, wheat meal or bran and rice bran or other derivatives of plant-based food production or processing operations. Suitable oilseed meals may include, without limitation, soybean, rapeseed/canola, sunflower, palm kernel, copra, linseed, peanut and sesame seed meals.

In some embodiments, the animal feed compositions comprise a fermented plant-based meal, such as fermented soybean meal. Soybean meal contains a variety of antinutritional factors (ANFs), such as trypsin inhibitor, phytate, lectins, and soya globulins, which limits its utilization as a plant-derived protein source for animal feed, especially for young animals. Fermentation using bacteria or fungi has been shown to improve the nutritional value of soybean meal, resulting in the degradation of various anti-nutritional factors and increasing the availability of small peptides and amino acids. Feeding non-ruminants with fermented soybean meal (as compared to unfermented soybean meal) offers several benefits, including increased average daily gain, improved growth performance, better protein digestibility, decreased immunological reactivity, and reduced undesirable morphological changes (Asian Australas. J. Anim. Sci. (2016) 29:1523-1529). Several studies have demonstrated that fermented soybean meal can be used to improve performance in broiler chickens. For example, feeding chicks soybean meal fermented with *Aspergillus oryzae* has been shown to significantly increase the average daily weight gain and average daily feed intake of the chicks as compared to standard soybean meal (Anim. Feed Sci Tech (2007) 134:235-242), and dietary supplementation with soybean meal fermented with *Aspergillus niger* has been shown to increase body weight, improve feed conversion ratio, and reduce feed consumption in broiler chickens (Int. J. Poult. Sci. (2006) 5(9):868-872). Further, fermentation with *Aspergillus usamii* almost completely degrades phytate phosphorus in soybean meal, and has been shown to improve phosphorus bioavailability in chicken feed (Poult Sci (1998) 77(4):552-6). The soybean meal may be fermented as discussed in the references above or alternatively may be fermented with the *Bacillus* strains provided herein prior to pelleting to produce a *Bacillus* fermented soybean meal based food. The *Bacillus* strains would sporulate as fermentation is complete and become part of the fermented soybean meal food product.

Other common plant-based components found in animal feeds for example may include, without limitation, cereal grains such as corn, wheat, sorghum, barley, rye, triticale, or oats. These plant-based components may include one or more anti-nutritional factors. As used herein, an "anti-nutritional factor" is a poorly digestible carbohydrate or protein that may reduce the metabolizable energy (ME) or phosphorus or amino acid availability within a feed composition. Suitable anti-nutritional factors may include, without limitation, α-galactosides (e.g., raffinose, stachyose, and verb ascose), cellulose, hemicellulose, galactomannan, arabinoxylans, xylose, phytate, lectins, trypsin inhibitors and other enzyme-inhibiting or antigenic proteins (e.g., β-conglycinin).

In some embodiments, the animal feed composition may be a poultry feed composition. As used herein, a "poultry feed composition" is poultry feed commonly used to raise poultry. Exemplary poultry feed compositions are well-described in the art and may be found, for example, in Scott's Nutrition of the Chicken 4th Edition, written by Steven Leeson and John D. Summers, University Books Guelph, Ontario, Canada 2001.

In some embodiments, the animal feed composition may be a low energy diet (LED) feed composition. A LED feed would contain lower inclusion levels of concentrated energy sources, such as supplemental lipids, compared with standard poultry feeds. Additionally, LED feeds could contain higher concentrations of dietary fiber. In some embodiments, the LED feed has 1-10% lower, 2-8% lower, or preferably 3-5% lower energy content (e.g., measured as kcal/kg') as compared to a standard poultry feed. In particular embodiments, the LED feed has about 4% lower energy content as compared to a standard poultry feed.

A standard poultry diet may vary greatly based on several factors, such as the age, breed, and intended use of the poultry (e.g., egg laying vs. meat production). For example, different methods are used to feed chickens that are raised for the production of eggs for human consumption (e.g., Leghorn-type), which have a small body size and are prolific layers, as opposed to chickens used as broilers or broiler breeders (meat-type), which have rapid growth rates and a large body size. Poultry are commonly fed on a three to five phase diets. For example, a three phase feeding program might include starter, grower, and finisher feeds, with the starter diet containing the highest level of protein and fed soon after hatching (from roughly 0-2 weeks). Then the chickens are switched to a "grower" diet (2-4 weeks), and finally to a "finisher" diet (4-6 weeks), in which the protein content is lower than starter because as the birds grow, their protein requirements decrease while their energy requirements increase. Thus, as used herein, the term "standard poultry diet" refers to a diet that would be considered appropriate for the particular bird and purpose at hand. The *Bacillus* isolate may be within the animal feed composition at a concentration ranging from between about $10^4$-$10^{12}$ cells/spores of the *Bacillus* isolate per gram of total animal feed composition, or any range therein. Suitably, between $10^4$ and $10^9$, or between $10^5$ and $10^8$, or between $10^6$ and $10^7$ spores per gram are used in the feed.

Methods

Methods for Improving Nutritional Uptake

In a still further aspect, the present invention relates to methods for improving nutritional uptake in a subject. The methods may include administering to the subject an effective amount of any of the compositions (*Bacillus* isolates, probiotic compositions, or animal feed compositions) described herein.

Improved nutritional uptake may be demonstrated by, for example, improved body weight gain in a subject, improved cumulative feed conversion ratio, or improved carcass characteristics in a subject as compared to a control subject. The Feed Conversion Ratio (FCR) is the metric for conversion of feed to body weight gain (feed intake/body weight gain). Improvements in feed conversion are attributed to improved absorption of nutrients by the animal. This can mean that the animal is better able to absorb nutrients because of a change in digestion and absorptive capacity resulting in more available nutrients in the gastrointestinal tract of the animal. With this measurement, a lower number/ratio is better than a higher one. Body weight/body weight gain (BW or BWG) is a measure of the growth rate and is increased when the overall health of the animal is improved (less resources spent on stress or disease), the gastrointestinal tract of the animal is working more optimally, more nutrients are made available to the animal, and/or feed intake increases. Carcass characteristics include both the weight and yield percentage (i.e., percent of live animal weight) of the hot carcass, hot fat pad, and chilled carcass. "Hot carcass" weights and yields are based on defeathered carcasses, with the neck, head, feet, and viscera removed, immediately after processing and before chilling. "Hot fat pad" weight and yield reflect abdominal fat tissue which is a reliable indicator of total body fat content. "Chilled carcass" weights and yields are based on carcasses after being placed in ice water for a four-hour chill. Carcass weights and yields may also be determined for specific body parts. For example, breast weight and yield are determined after cutting the pectoralis major from the chilled carcass, while tender weights and yield are determined from cutting the pectoralis minor from the chilled carcass. Total white meat is the sum of the pectoralis major and pectoralis minor weights, as white meat is the most expensive and desirable cut of chicken in the U.S. market, and an increase in yield is profitable to the industry. These measurements are typically used in part to determine the quality of a feed product. Feed intake (FI) is a measure of the amount of feed eaten by the animal. Thus, at equal BW, a lower FI number is better and indicates that the animal is more efficiently converting feed to body weight, resulting in a lower FCR.

As used herein, "administering" may be carried out through any of the variety of procedures used to apply compositions to a subject that will be apparent to the skilled artisan. Suitable application methods may include incorporating composition into the feed or water source for the subject. Accordingly, the compositions used in accordance with the present methods may be any one of compositions disclosed herein. In some embodiments, the composition of the present methods may be a liquid including water such as drinking water that may be given to the subject. In other embodiments, the composition is a dry food composition or a pelleted feed composition. In these embodiments *Bacillus* spores may be added as a dry powder to the feed either before or after pelleting of the feed.

As used herein, a "subject" may include any animal species. Suitable subjects may include, without limitation, a poultry species, a cow species, a pig species, a sheep species, a goat species, a fish species, or a mammalian species such as human and non-human mammalian species. Preferably, the subject is a poultry species such as a chicken or turkey species.

In accordance with the present methods, the body weight gain of the agricultural animal species may be improved by increasing by at least 5%, 10%, 20%, or 30% the body weight of the agricultural animal as compared to a control animal.

As used herein, a "control subject" or "control animal" refers to an animal species that is given a composition that excludes the *Bacillus* isolates described herein. Suitably, the control animal is fed a similar food product without any bacterial component added or without the specific isolates described herein. For example, an appropriate control animal for a chicken species that is subjected to the present methods would be the same chicken species fed a composition that excludes the *Bacillus* isolate.

In accordance with the present methods, the cumulative feed conversion ratio of the subject may be improved by decreasing the cumulative feed conversion ratio by at least 5%, 10%, 20%, 30%, 40%, or 50% as compared to a control subject.

Methods for Producing an Animal Feed Composition

In another aspect, the present invention relates to methods for producing an animal feed composition. The methods may include introducing any one of the *Bacillus* isolates or probiotic compositions described herein into any of the animal feed compositions described herein.

Optionally, the methods may further include pelleting the animal feed composition. In such embodiments, the *Bacillus* isolate or probiotic composition is introduced into the animal feed composition prior to, concurrently, or after the pelleting of the animal feed composition. For use in these processes, the *Bacillus* may be used in spore form.

Methods for Preventing Footpad Dermatitis

In another aspect, the present invention provides methods for reducing the incidence of footpad dermatitis (FPD) in poultry. The methods involve administering to the poultry an effective amount of any of the compositions (*Bacillus* isolates, probiotic compositions, or animal feed compositions) described herein.

FPD, also known as pododermatitis, is a condition characterized by lesions on the feet of poultry caused by ammonia burns. Ammonia is produced by a combination of excess litter moisture and nitrogen, both of which are increased in birds fed diets with elevated levels of galactooligosaccharides and non-starch polysaccharides (e.g., high soybean meal or alternative grain diets). Chicken paws are a major export for U.S. poultry integrators, and a reduction in paw condemnations at the processing plant increases profitability. Importantly, FPD is a threat to the health and welfare of the birds, so decreasing its incidence improves well-being. FPD is commonly assessed using a subjective scoring system. For instance, the inventors used a 0-2 rating scale to compare the incidence of FPD across groups of chickens, and found that there was a reduced incidence of FPD in chickens that were fed at least one *Bacillus* isolate (isolate 46 or a combination of isolate 46 and isolate 40) as compared to chicken that were not fed a *Bacillus* isolate (see Table 11).

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 0.01% to 5%, it is intended that values such as 0.025% to 0.50%, 0.10% to 1.0%, or 0.025% to 0.075%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The following examples are meant only to be illustrative and are not meant as limitations on the scope of the invention or of the appended claims.

EXAMPLES

Selection of Direct Fed Microbials (DFMs) for In Situ Diminution of Anti-Nutritional Factors Associated with Non-Starch Polysaccharides (NSP) and Free Sugars in the Diet of Monogastric Animals Example 1—In Vitro Isolate Screening

*Bacillus* isolates were obtained from fecal samples gathered from various poultry flocks. The various poultry flocks included five separate flocks. The age of the chicken flocks ranged from 29 to 65 weeks old and the turkey flocks ranged from 16 to 18 weeks old. We hypothesized that using fecal samples would increase the chances of finding host-adapted *Bacillus* isolates that have a niche within the chicken gastrointestinal tract. Candidate isolates were grown in solid state fermentation (SSF) media to ensure robust sporulation of 10^10 or 10^11 spores/gram to confirm their ability to be mass-produced commercially. The spores were also tested under extreme heat conditions to ensure heat stability for the pelleting process of commercial feed production. The isolates were exposed to 90° C. for 10 minutes, which is the maximum temperature during the pelleting process and for a much longer duration than the typical pelleting process. Isolates were also selected based on biofilm production, which is important for survival and replication within the bird.

Following isolation, the *Bacillus* isolates were screened for galactosidase, cellulase, xylanase, and beta-mannase activities. Galactosidase activity was evaluated using a simple plate media with raffinose as the sole source of energy to support growth of the organism. 10 µl of each isolate grown up in broth culture and drop plated onto the center of an ammonia media agar plate containing 0.2% raffinose as the only source of nutrition. As shown in Table 1, several of the *Bacillus* isolates exhibited galactosidase activity in this assay including isolates 26, 30, 31, 34, 36, 40, 46, 65, 86, 94, 96, 101, 102, and 105.

TABLE 1

*Bacillus* isolate growth on ammonia media plates containing 0.2% raffinose

| Isolate | Growth on ammonia media plates containing 0.2% raffinose |
|---|---|
| 8 | − |
| 26 | + |
| 30 | + |
| 31 | + |
| 34 | + |
| 36 | + |
| 37 | − |
| 40 | + |
| 43 | − |
| 46 | + |
| 49 | − |
| 51 | − |
| 53 | − |
| 56 | − |
| 57 | − |
| 61 | − |
| 62 | − |
| 65 | + |
| 74 | − |
| 75 | − |
| 86 | + |
| 92 | − |
| 94 | + |
| 96 | + |
| 101 | + |
| 102 | + |
| 105 | + |
| 112 | − |

Cellulase, xylanase, and beta-mannase activities of candidate isolates were evaluated using insoluble dyed substrates in agar plates. These insoluble substrates rapidly hydrate to form gel particles which are readily and rapidly hydrolyzed by specific enzymes, releasing soluble dye-labelled fragments.

To test for xylanase activity, we used soft agar overlays consisting of ammonia media containing only high purity dyed, crosslinked and finely milled insoluble AZCL-Arabinoxylan (Wheat) for identification of enzyme activity. A change in coloration when compared to the test plate indicates that the isolate is capable of enzymatically hydrolyzing the carbohydrate included in the overlay as its only means of nutrition. As shown in FIG. 1 and Table 2, isolates 26, 30, 31, 34, 36, 40, 46, 65, 86, 94, 96, 101, 102, and 105 exhibited xylanase activity.

TABLE 2

Bacillus Isolate Growth on Ammonia Media Plates with
0.0125% glucose with an Arabinoxylan soft agar overlay

| Isolate | Growth on ammonia media plates with 0.0125% glucose with an Arabinoxylan soft agar overlay |
|---|---|
| Test | − |
| 26 | + |
| 30 | + |
| 31 | + |
| 34 | + |
| 36 | + |
| 40 | + |
| 46 | + |
| 65 | + |
| 86 | + |
| 94 | + |
| 96 | + |
| 101 | + |
| 102 | + |
| 105 | + |

Figure 2:
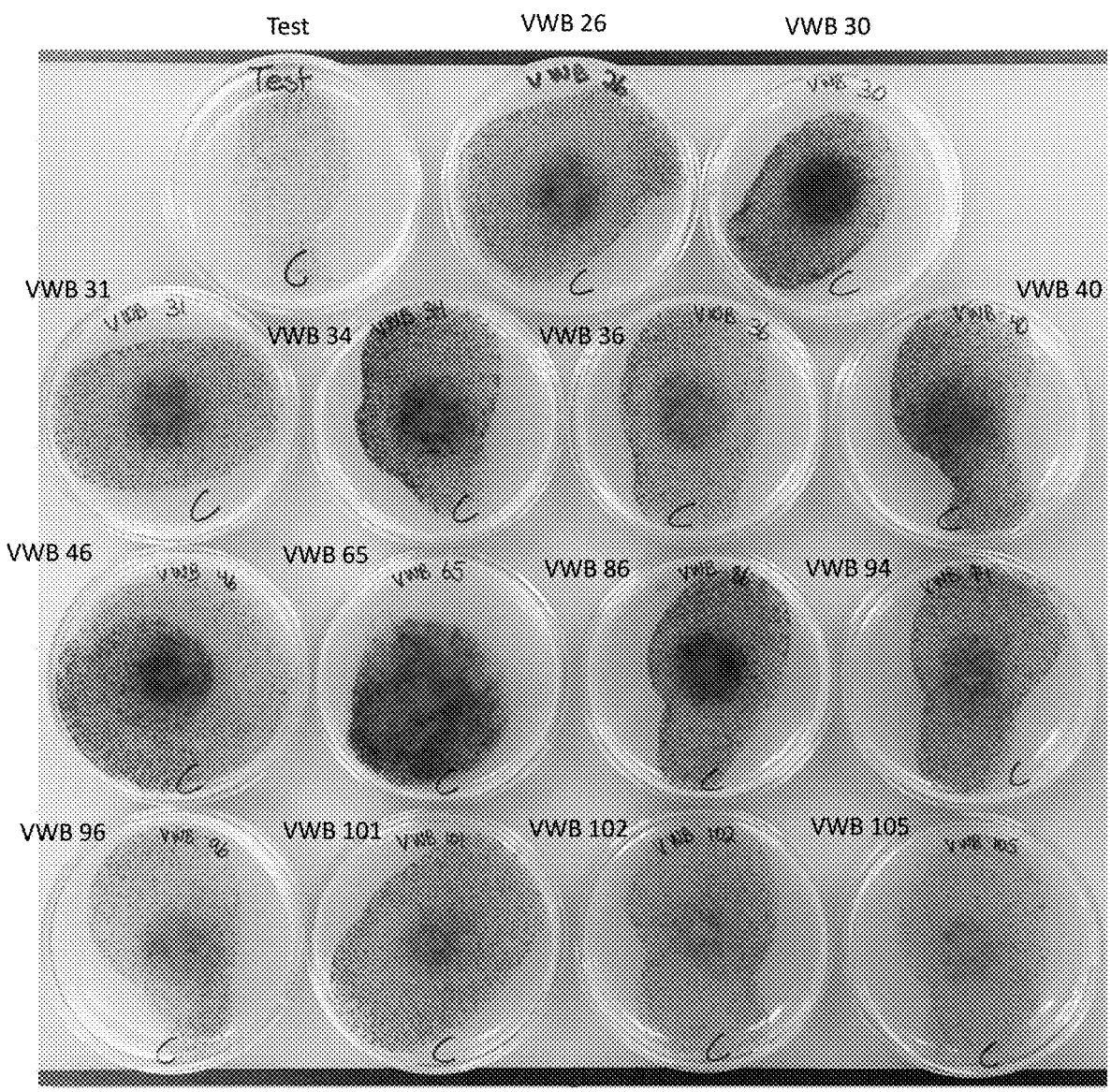
FIG. 2 shows isolate growth on ammonia media plates containing 0.0125% glucose with cellulose soft agar overlays.

To test for cellulase activity, we used soft agar overlays consisting of ammonia media containing only high purity dyed, crosslinked and finely milled insoluble AZCL-HE-Cellulose for identification of enzyme activity. A change in coloration when compared to the test plate indicates that the isolate is capable of enzymatically hydrolyzing the carbohydrate included in the overlay as its only means of nutrition. As shown in FIG. 2 and Table 3, isolates 26, 30, 31, 34, 36, 40, 46, 65, 86, 94, 96, 101, 102, and 105 exhibited cellulase activity.

TABLE 3

Bacillus Isolate Growth on Ammonia Media Plates with
0.0125% glucose with a Cellulose soft agar overlay

| Isolate | Growth on ammonia media plates with 0.0125% glucose with a Cellulose soft agar overlay |
|---|---|
| Test | − |
| 26 | + |
| 30 | + |
| 31 | + |
| 34 | + |
| 36 | + |
| 40 | + |
| 46 | + |
| 65 | + |
| 86 | + |
| 94 | + |
| 96 | + |
| 101 | + |
| 102 | + |
| 105 | + |

Figure 3:
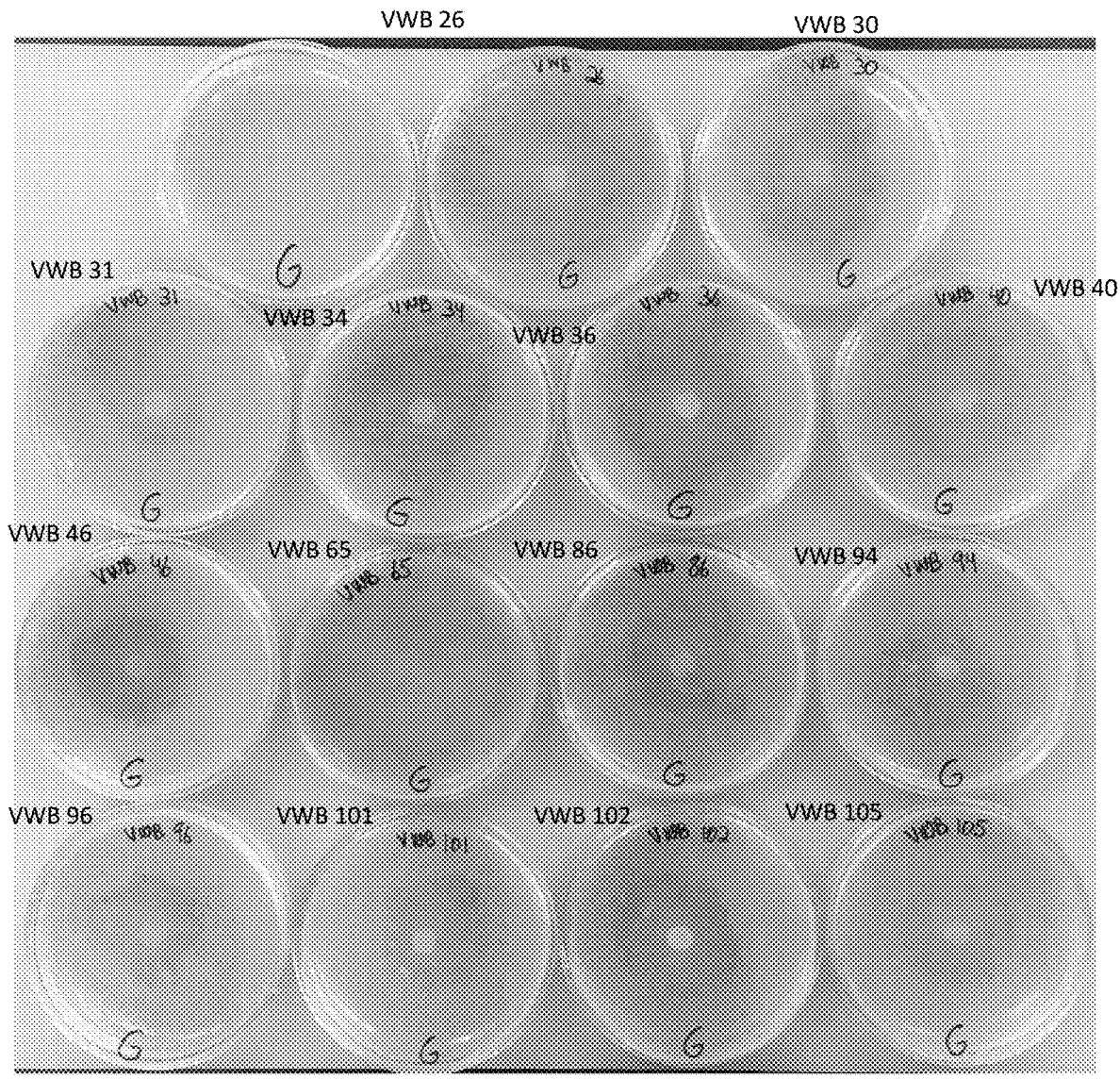
FIG. 3 shows isolate growth on ammonia media plates containing 0.0125% glucose with galactomannan soft agar overlays.

To test for beta-mannase activity, soft agar overlays consisted of ammonia media containing only high purity dyed, crosslinked and finely milled insoluble galactomannan. RedCL-Galactomannan (Carob) was used for identification of enzyme activity. A change in coloration when compared to the test plate indicates that the isolate is capable of enzymatically hydrolyzing the carbohydrate included in the overlay as its only means of nutrition. As shown in FIG. 3 and Table 4, isolates 26, 30, 31, 34, 36, 40, 46, 65, 86, 94, 96, 101, 102, and 105 exhibited beta-mannase activity.

TABLE 4

Bacillus Isolate Growth on Ammonia Media Plates with
0.0125% glucose with a Galactomannan Soft Agar Overlay

| Isolate | Growth on ammonia media plates with 0.0125% glucose with a Galactomannan soft agar overlay |
|---|---|
| Test | − |
| 26 | + |
| 30 | + |
| 31 | + |
| 34 | + |
| 36 | + |
| 40 | + |
| 46 | + |
| 65 | + |
| 86 | + |
| 94 | + |
| 96 | + |
| 101 | + |
| 102 | + |
| 105 | + |

Example 2—In Vivo Testing of Bacillus Isolates

In vivo experiments using the Bacillus isolates (i.e, isolates 31, 40, 46, and 65) identified above were performed to determine the effectiveness of the isolate in a low energy corn and soybean meal based diet fed to broiler chickens. The Bacillus isolates were added to the feed premix prior to the mixing of the individual treatments to ensure proper distribution of the spores throughout the feed. Spores were added to the feed at a quantity that would ensure a final spore count of approximately $10^6$ in the finished feed. Birds were provided feed ad libitum for the life of the trial with the respective spore treatment groups receiving spores for the duration of the trial. Birds were reared in floor pens or battery cages and under standard commercial management practices. Several parameters were measured in the in vivo trials at days 7, 14, and 21. There was a 125 kcal/kg measured energy (ME) difference between the control, high energy diet (HED) and low energy diet (LED) used in these trials (Table 5).

TABLE 5

Ingredient and calculated nutrient composition (% as-fed) of the starter basal diets (high energy diet (HED) and low energy diet (LED)) for 21 d trials.

| | HED | LED |
|---|---|---|
| Ingredients (%) | | |
| Corn | 53.34 | 55.71 |
| Soybean Meal | 40.00 | 40.00 |
| Soy Oil | 2.88 | 0.53 |
| Dicalcium Phosphate | 1.67 | 1.66 |
| Limestone | 0.99 | 1.00 |
| DL-methionine | 0.27 | 0.27 |
| L-lysine HCL | 0.07 | 0.06 |
| L-threonine | 0.05 | 0.04 |
| Salt | 0.69 | 0.69 |
| Vitamin premix | 0.10 | 0.10 |
| Mineral premix | 0.10 | 0.10 |
| Choline Chloride (60%) | 0.05 | 0.05 |
| Se Premix (0.06%) | 0.02 | 0.02 |
| Santoquin | 0.02 | 0.02 |
| Inert Filler[1] | 0.02 | 0.02 |

TABLE 5-continued

Ingredient and calculated nutrient composition (% as-fed) of the starter basal diets (high energy diet (HED) and low energy diet (LED)) for 21 d trials.

| | HED | LED |
|---|---|---|
| Calculated analysis | | |
| $AME_n$, kcal/kg[2] | 3,050 | 2,925 |
| CP (%) | 23.62 | 23.79 |
| dLys (%)[3] | 1.20 | 1.22 |

[1]Spores were added at the expense of sand
[2]$AME_n$ = Nitrogen corrected apparent metabolizable energy
[3]dLys = Digestible lysine A brief explanation of the significance of each measure is included here:

Feed Conversion Ratio (FCR): This is the metric for conversion of feed to body weight (Feed intake/body weight). Improvements in feed conversion are attributed to improved absorption of nutrients by the animal. This can mean that the animal is better able to absorb nutrients because of a change in absorptive capacity or more available nutrients in the gastrointestinal tract (GIT) of the animal. With this measurement, a lower number/ratio is better than a higher one.

Body weight/body weight gain (BW or BWG): growth rate is increased when the overall health of the animal is improved (less resources spent on stress or disease), the GIT is working more optimally, more nutrients are made available to the animal, and/or feed intake increases.

Feed intake (FI) is a measure of the amount of feed eaten by the animal. At equal BW, a lower number is better and indicates that the animal is more efficiently converting feed to body weight, resulting in a lower FCR.

Hot carcass weights and yields are based on defeathered carcasses, with the neck, head, feet, and viscera removed, immediately after processing and before chilling. Hot fat pad weight and yield reflect abdominal fat tissue which is a reliable indicator of total body fat content. Chilled carcass weights and yields are based on carcasses after being placed in ice water for a four-hour chill. Breast weight and yield are determined after cutting the pectoralis major from the chilled carcass. Tender weights and yield are determined from cutting the pectoralis minor from the chilled carcass. Total white meat is the sum of the pectoralis major and pectoralis minor weights, as white meat is the most expensive and desirable cut of chicken in the U.S. market, and an increase in yield is profitable to the industry.

Footpad dermatitis (FPD) is a condition characterized by lesions on the feet of poultry caused by a combination of excess litter moisture and nitrogen, leading to ammonia production. Moisture and nitrogen excretion are increased in birds fed diets with elevated levels of galactooligosaccharides and non-starch polysaccharides as seen with high soybean meal or alternative grain diets. The size of the associated lesions increase with severity and are subjectively scored on a scale from 0-2, in which a score of 0 indicates no lesions or very small superficial lesions, a score of 1 indicates mild lesions and discoloration of the footpad, and a score of 2 indicates severe lesions with ulcers or scabs and swollen foot pads. Chicken paws are a major export for U.S. poultry integrators, and a reduction in paw condemnations at the processing plant increases profitability. Importantly, FPD is a threat to the health and welfare of the birds, so decreasing its incidence improves well-being.

Figure 4:
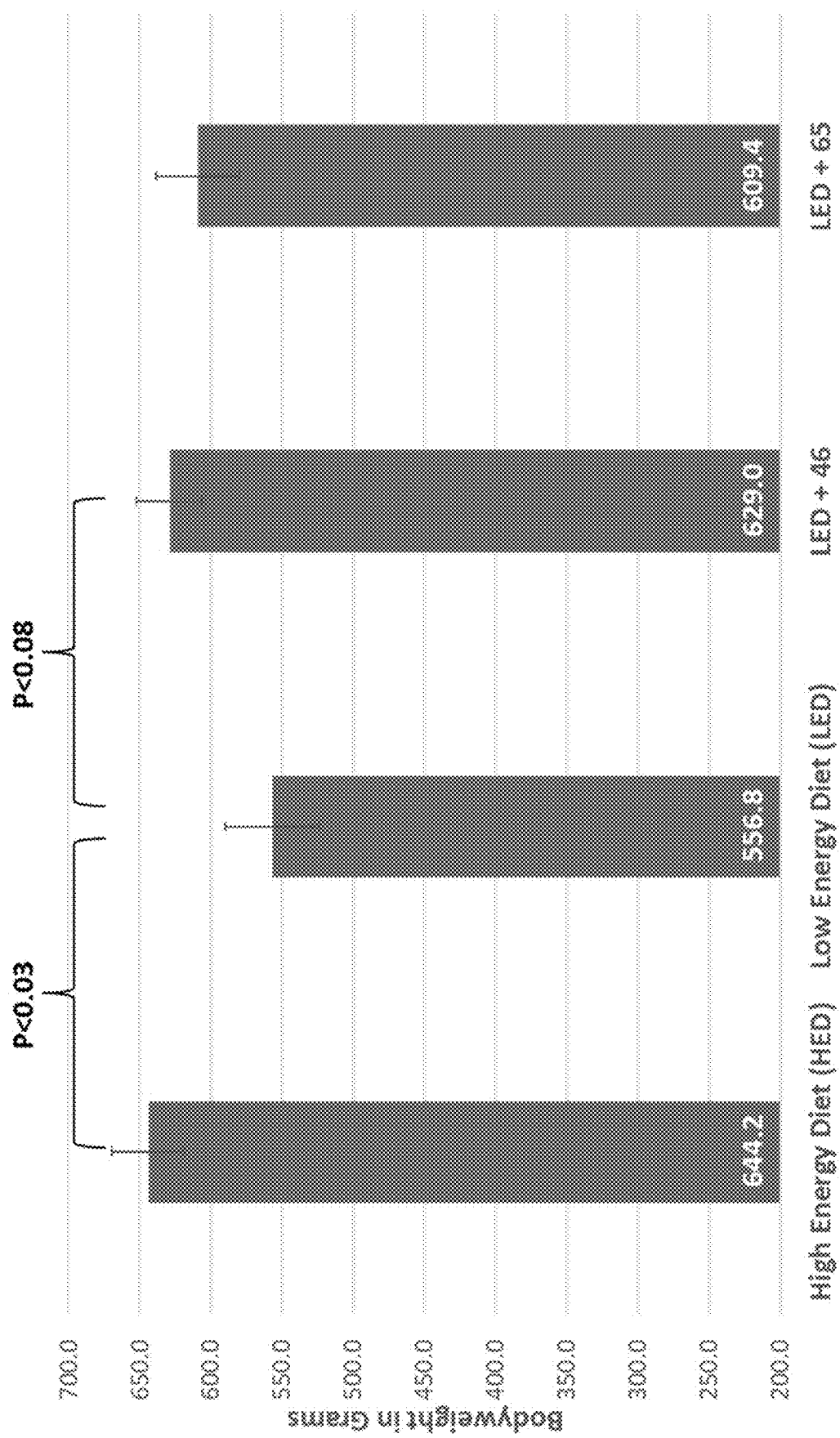
FIG. 4 shows average bird weight at day 21 of broilers fed a low energy diet with or without dietary inclusion of a *Bacillus* direct fed microbial.

In FIG. 4, the growth rate of birds fed a low energy diet supplemented with a *Bacillus* direct fed microbial were compared to birds fed only a low energy diet (LED) or a high energy diet (HED). Isolates used in this experiment consisted of isolates 46 and 65. LED+Isolate 46 and HED had a significant increase in average body weight at D21 when compared to the LED without *Bacillus* supplementation. Each P-value was generated from a T-test against the LED.

Figure 5:
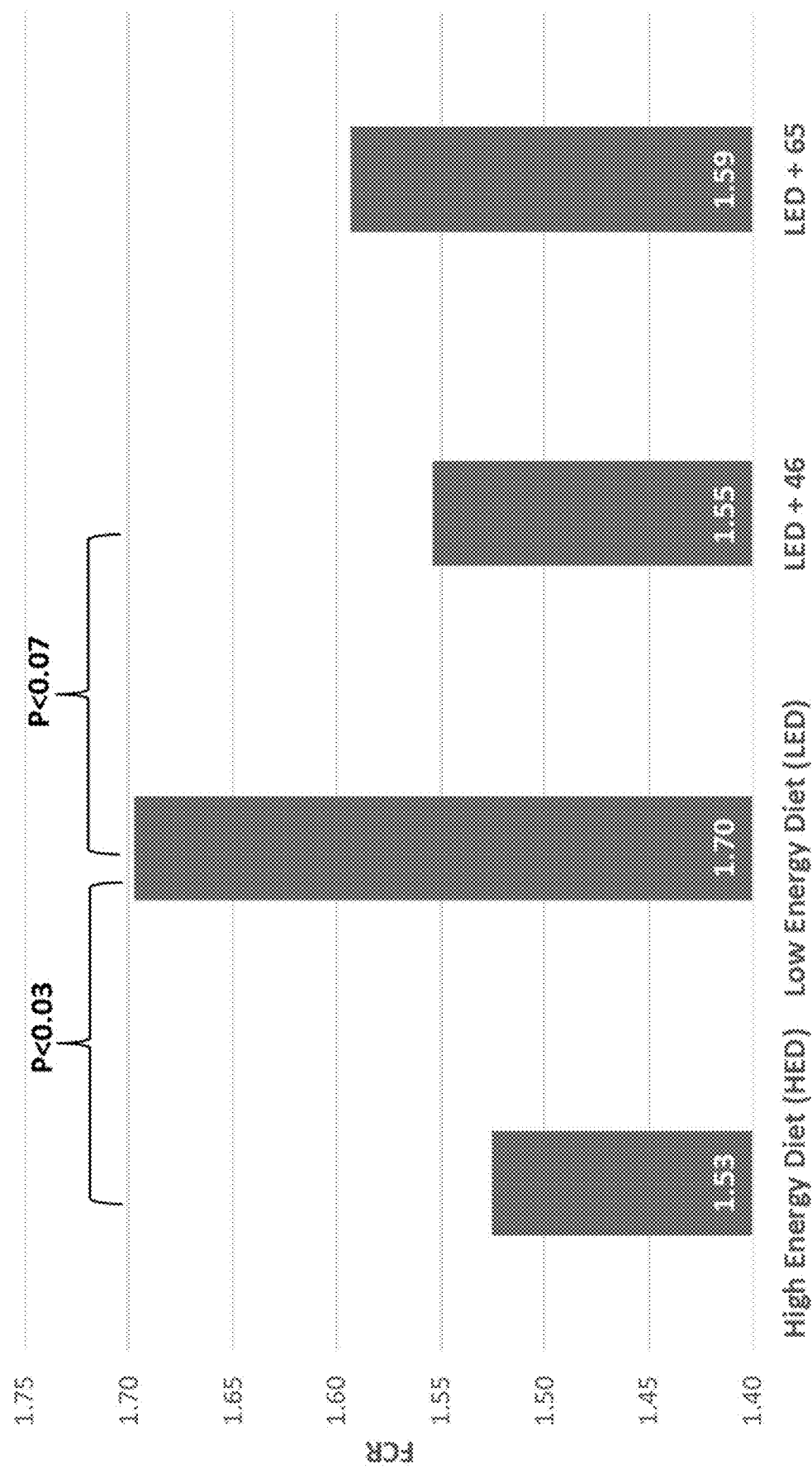
FIG. 5 shows the feed conversion ratio (D1-21) of broilers fed a low energy diet with or without dietary inclusion of a *Bacillus* direct fed microbial.

In FIG. 5, the feed conversion ratio of birds fed a low energy diet supplemented with a *Bacillus* direct fed microbial were compared to birds fed only a low energy diet (LED) or a high energy diet (HED). Isolates used in this experiment consisted of isolates 46 and 65. LED+Isolate 46 and HED had a significant decrease in feed conversion ratio from D1-21 when compared to the low energy diet without *Bacillus* supplementation. Each P-value was generated from a T-test against the LED.

Figure 6:
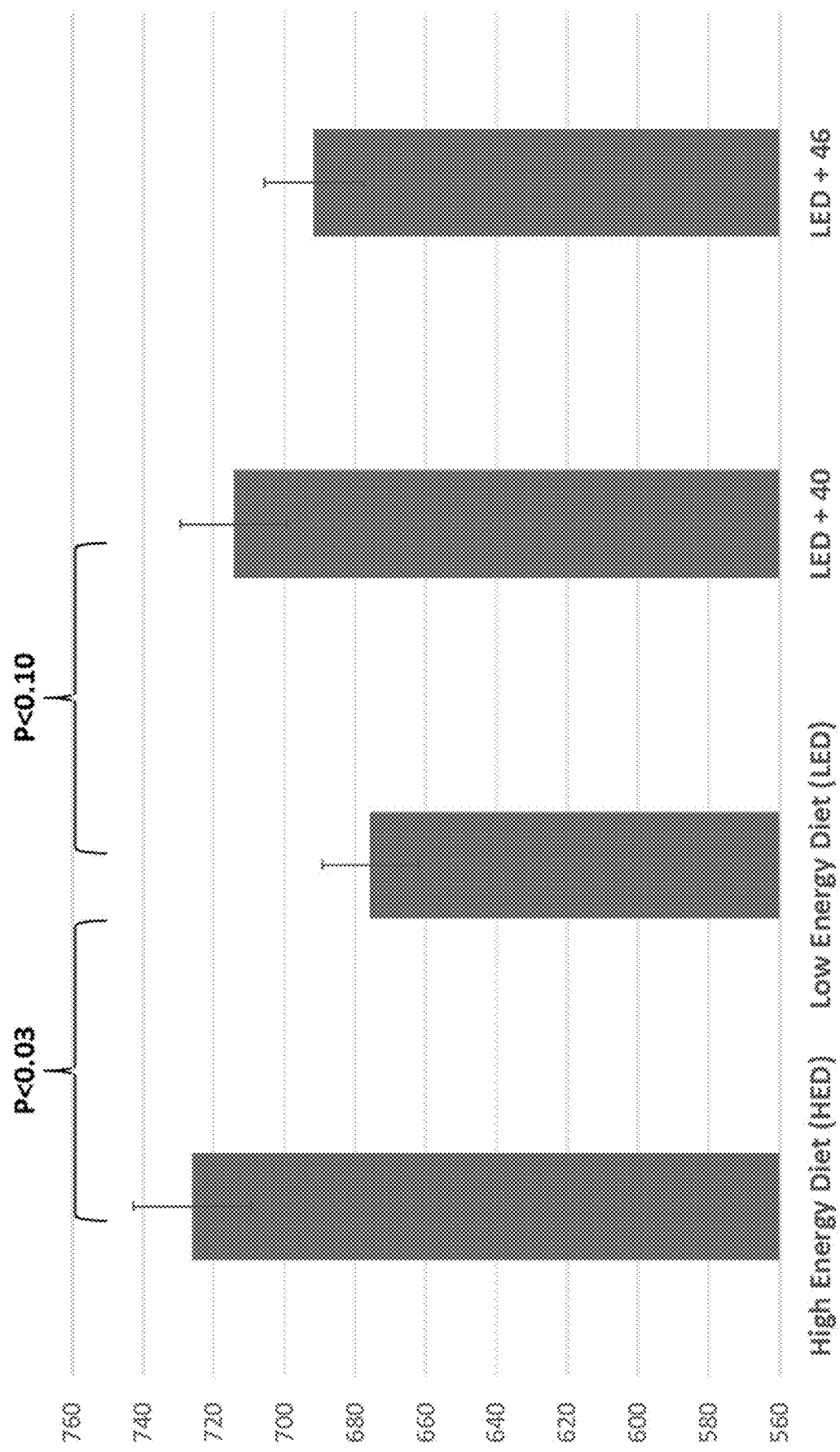
FIG. 6 shows average bird weight at day 21 of broilers fed a low energy diet with or without dietary inclusion of a *Bacillus* direct fed microbial.

In FIG. 6, the growth rate of birds fed a low energy diet supplemented with a *Bacillus* direct fed microbial were compared to birds fed only a low energy diet (LED) or a high energy diet (HED). Isolates used in this experiment consisted of isolates 40 and 46. LED+isolate 40 and HED had a significant increase in average body weight at D21 when compared to the LED without *Bacillus* supplementation. Each P-value was generated from a T-test against the LED.

Figure 7:
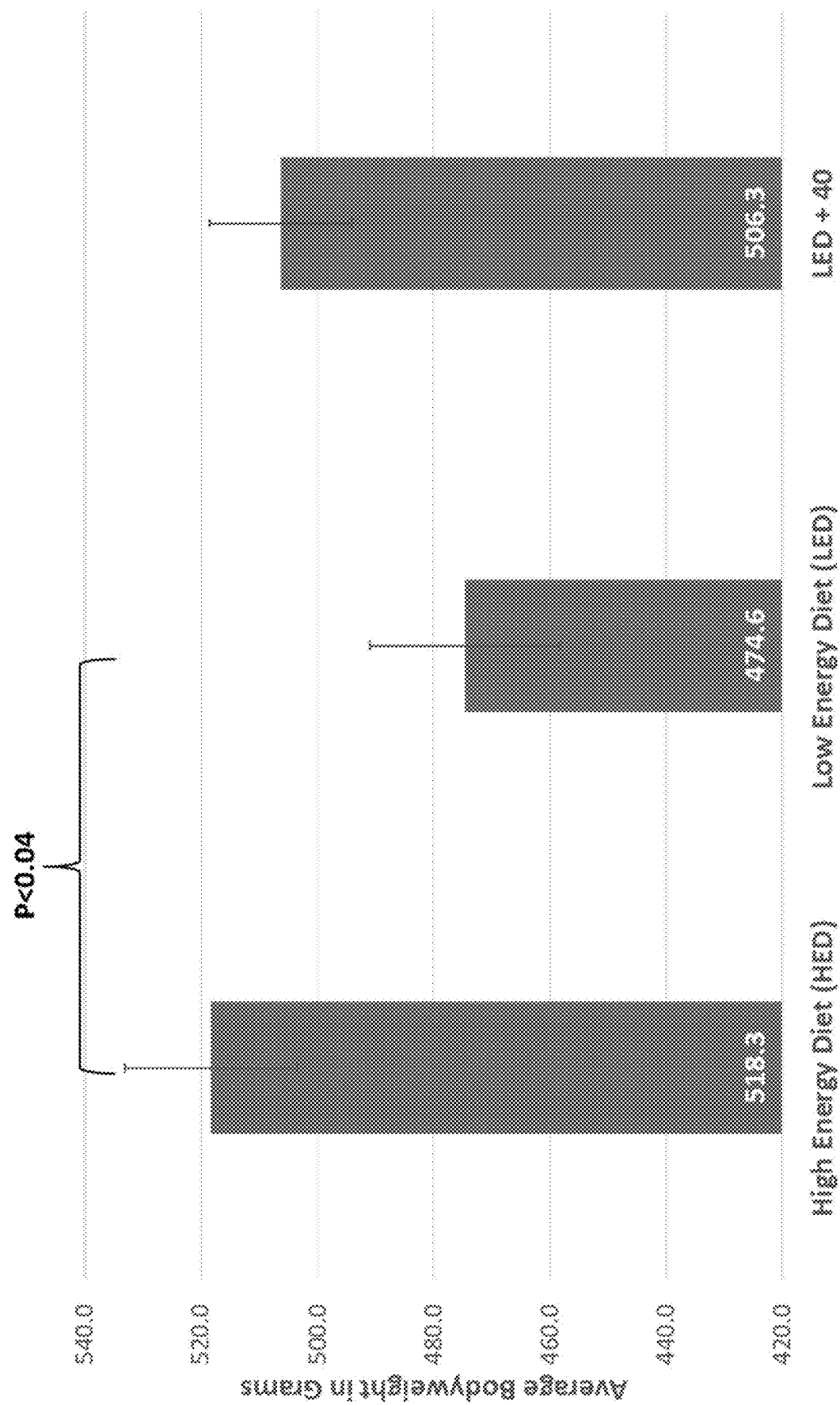
FIG. 7 shows average bird weight at day 21 of broilers fed a low energy diet with or without dietary inclusion of a *Bacillus* direct fed microbial.

In FIG. 7, the growth rate of birds fed a low energy diet supplemented with a *Bacillus* direct fed microbial were compared to birds fed only a low energy diet (LED) or a high energy diet (HED). The isolate used in this experiment consisted of isolate 40. HED had a significant increase in average body weight at D21 when compared to the LED without *Bacillus* supplementation. Each P-value was generated from a T-test against the LED.

Figure 8:
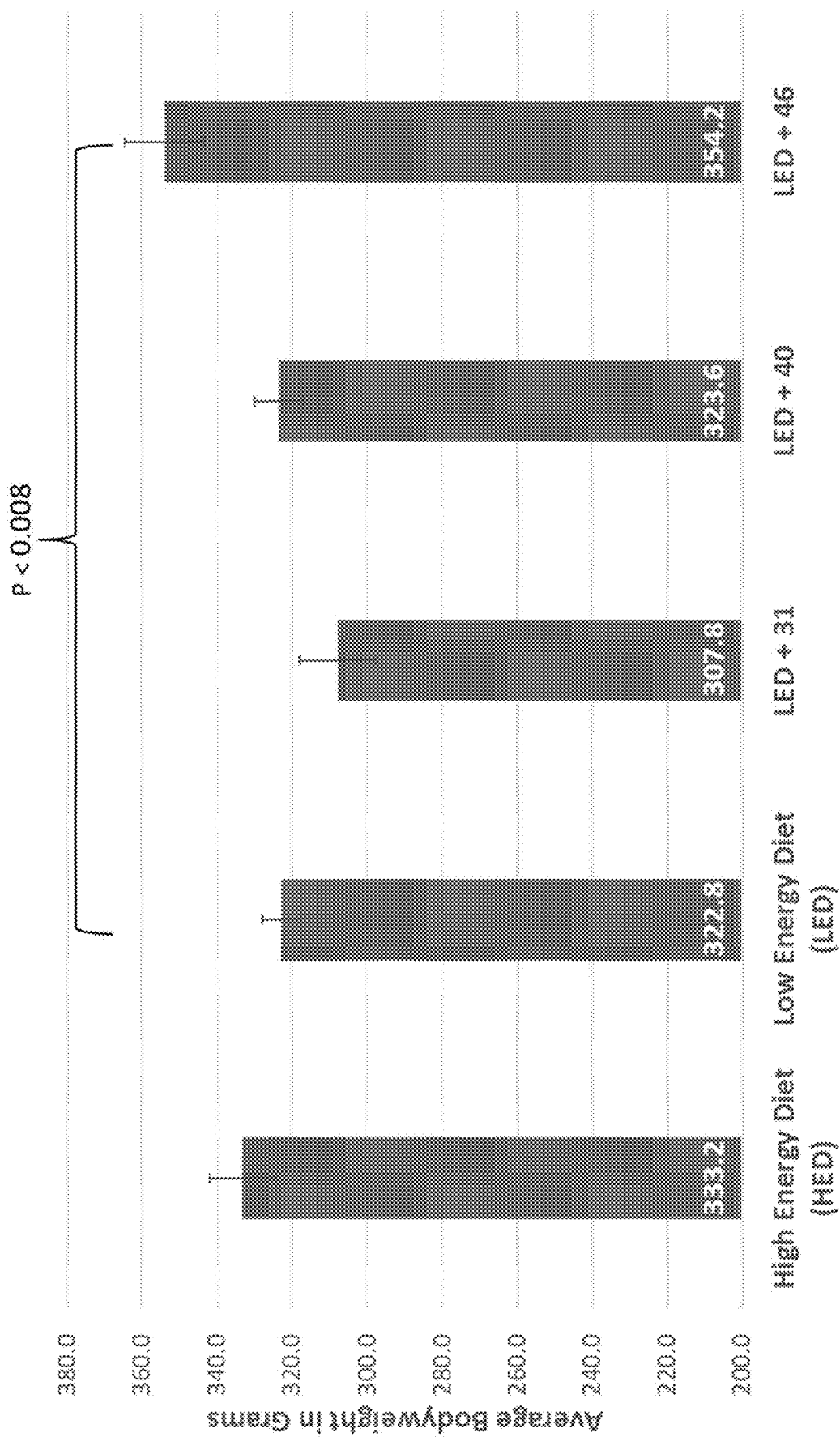
FIG. 8 shows average bird weight at day 14 of broilers fed a low energy diet with or without dietary inclusion of a *Bacillus* direct fed microbial.

In FIG. 8, the growth rate of birds fed a low energy diet supplemented with a *Bacillus* direct fed microbial were compared to birds fed only a low energy diet (LED) or a high energy diet (HED) Isolates used in this experiment consisted of isolates 31, 40, and 46. LED+isolate 46 had a significant increase in average body weight at D14 when compared to the low energy diet without *Bacillus* supplementation. Each P-value was generated from a T-test against the LED.

Figure 9:
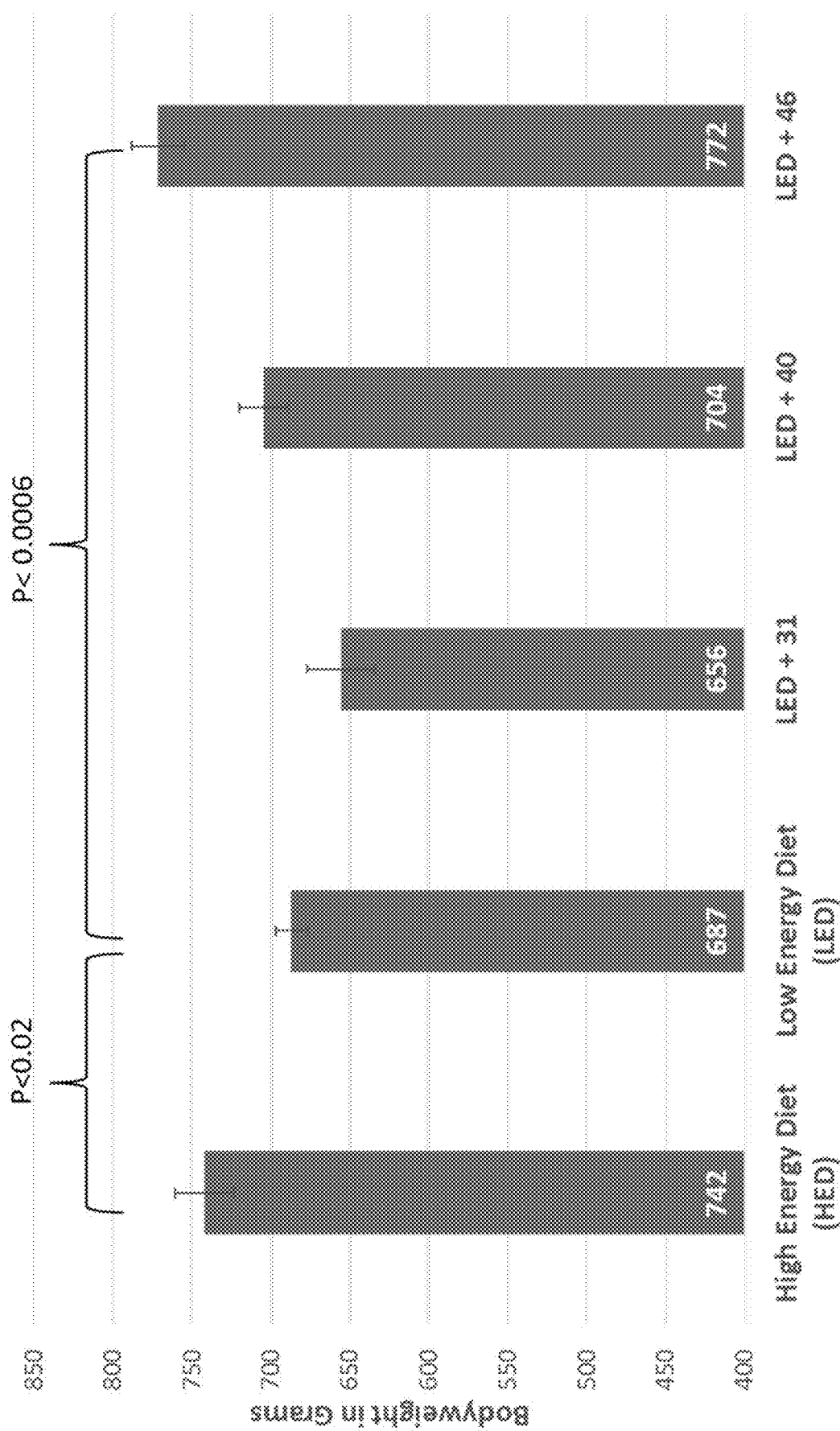
FIG. 9 shows average bird weight at day 21 of broilers fed a low energy diet with or without dietary inclusion of a *Bacillus* direct fed microbial.

In FIG. 9, the growth rate of birds fed a low energy diet supplemented with a *Bacillus* direct fed microbial were compared to birds fed only a low energy diet (LED) or a high energy diet (HED) Isolates used in this experiment consisted of isolates 31, 40, and 46. LED+isolate 46 and HED had a significant increase in average body weight at D21 when compared to the LED without *Bacillus* supplementation. Each P-value was generated from a T-test against the LED.

Figure 10:
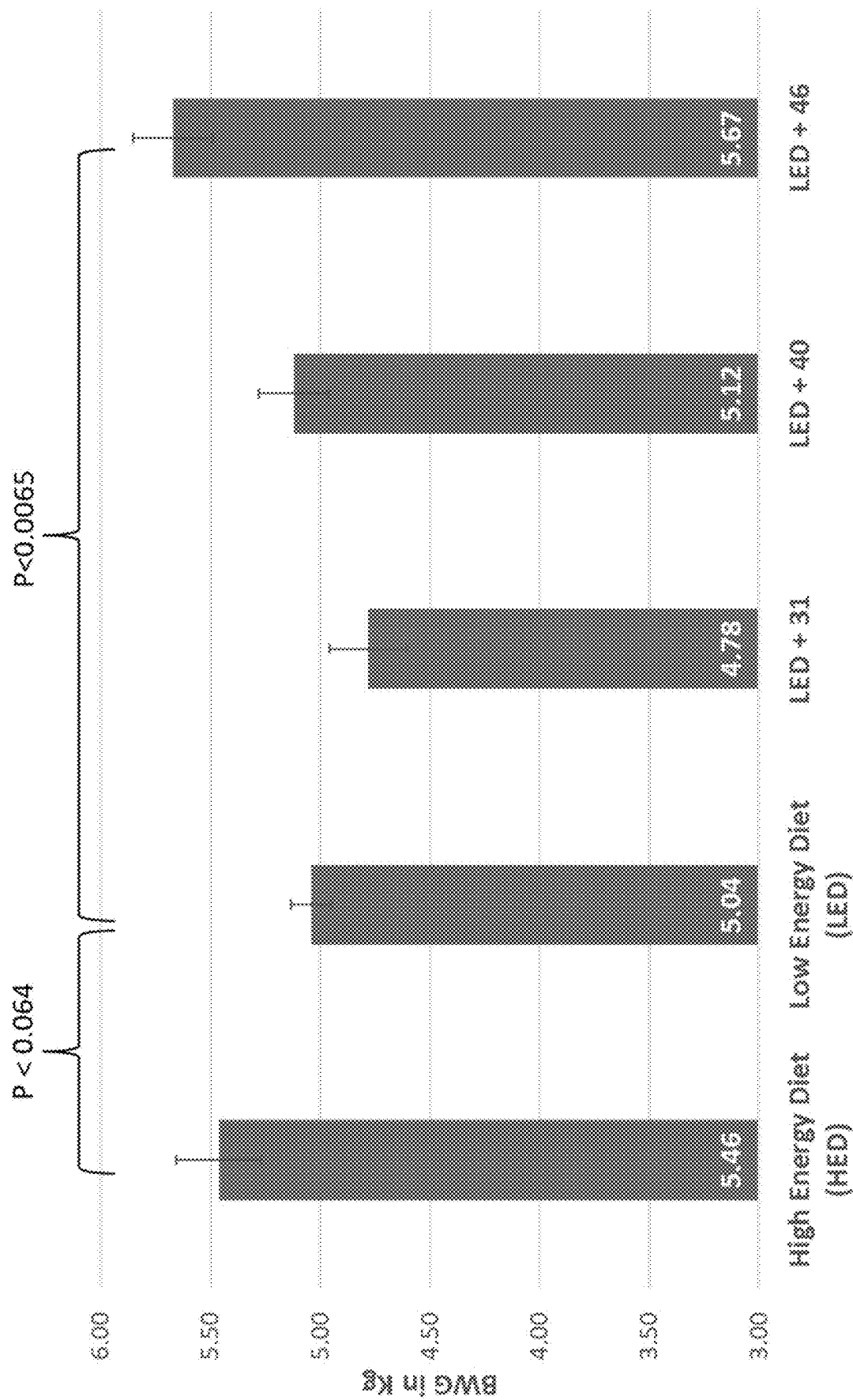
FIG. 10 shows body weight gain (BWG; D0-21) of broilers fed a low energy diet with or without dietary inclusion of a *Bacillus* direct fed microbial.

In FIG. 10, the body weight gain of birds fed a low energy diet supplemented with a *Bacillus* direct fed microbial were compared to birds fed only a low energy diet (LED) or a high energy diet (HED) Isolates used in this experiment consisted of isolates 31, 40, and 46. LED+isolate 46 and HED had a significant increase in body weight gain from D0-21 when compared to the LED without *Bacillus* supplementation. Each P-value was generated from a T-test against the LED.

Figure 11:
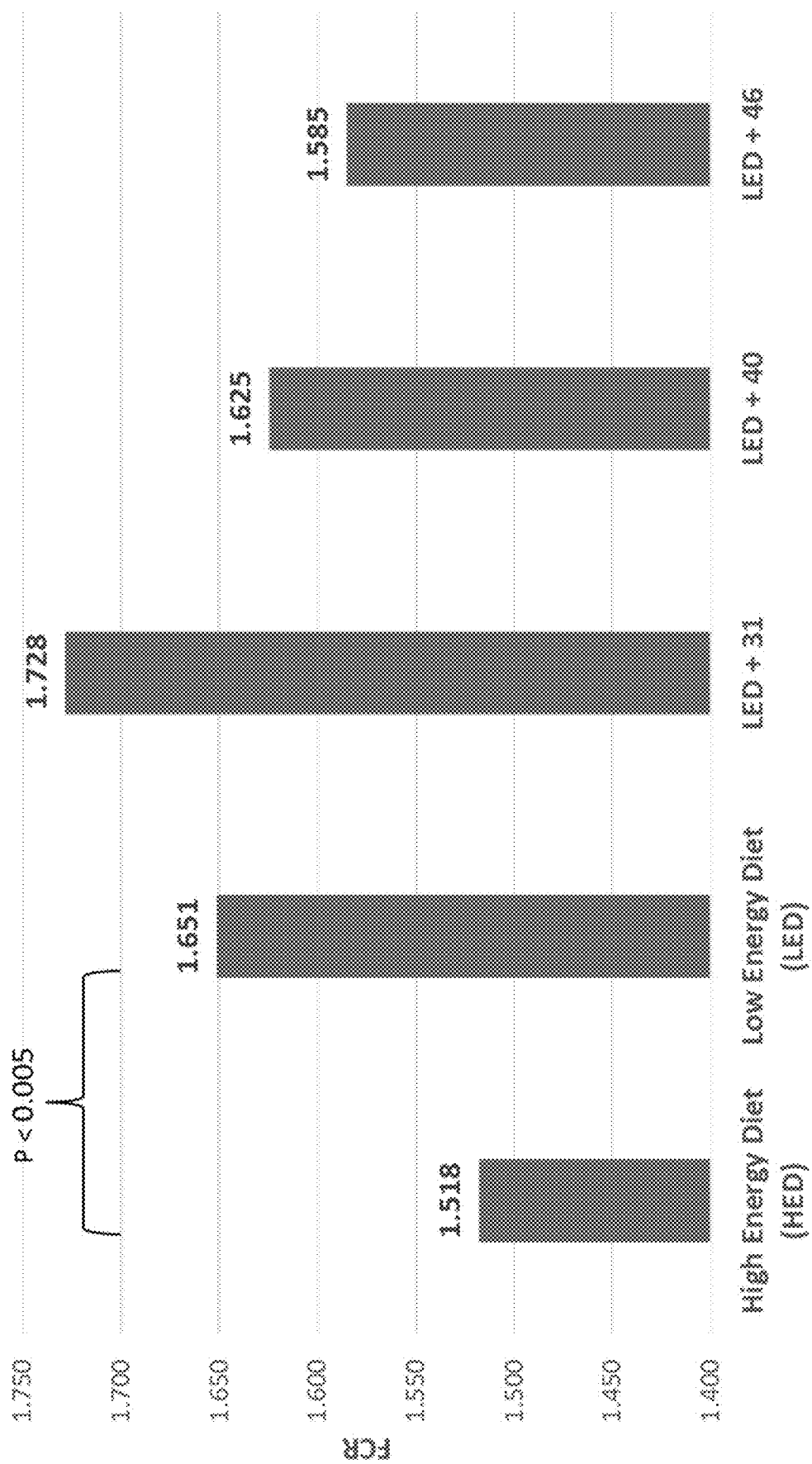
FIG. 11 shows feed conversion ratio (FCR; D0-21) of broilers fed a low energy diet with or without dietary inclusion of a *Bacillus* direct fed microbial.

In FIG. 11, the feed conversion ratio of birds fed a low energy diet supplemented with a *Bacillus* direct fed microbial were compared to birds fed only a low energy diet (LED) or a high energy diet (HED) Isolates used in this experiment consisted of isolates 31, 40, and 46. HED had a significant decrease in feed conversion ratio from D0-21 when compared to the low energy diet without *Bacillus* supplementation. Each P-value was generated from a T-test against the LED. The group fed a LED diet and isolate 46 was intermediate between the HED and the LED groups which were statistically different.

Figure 12:
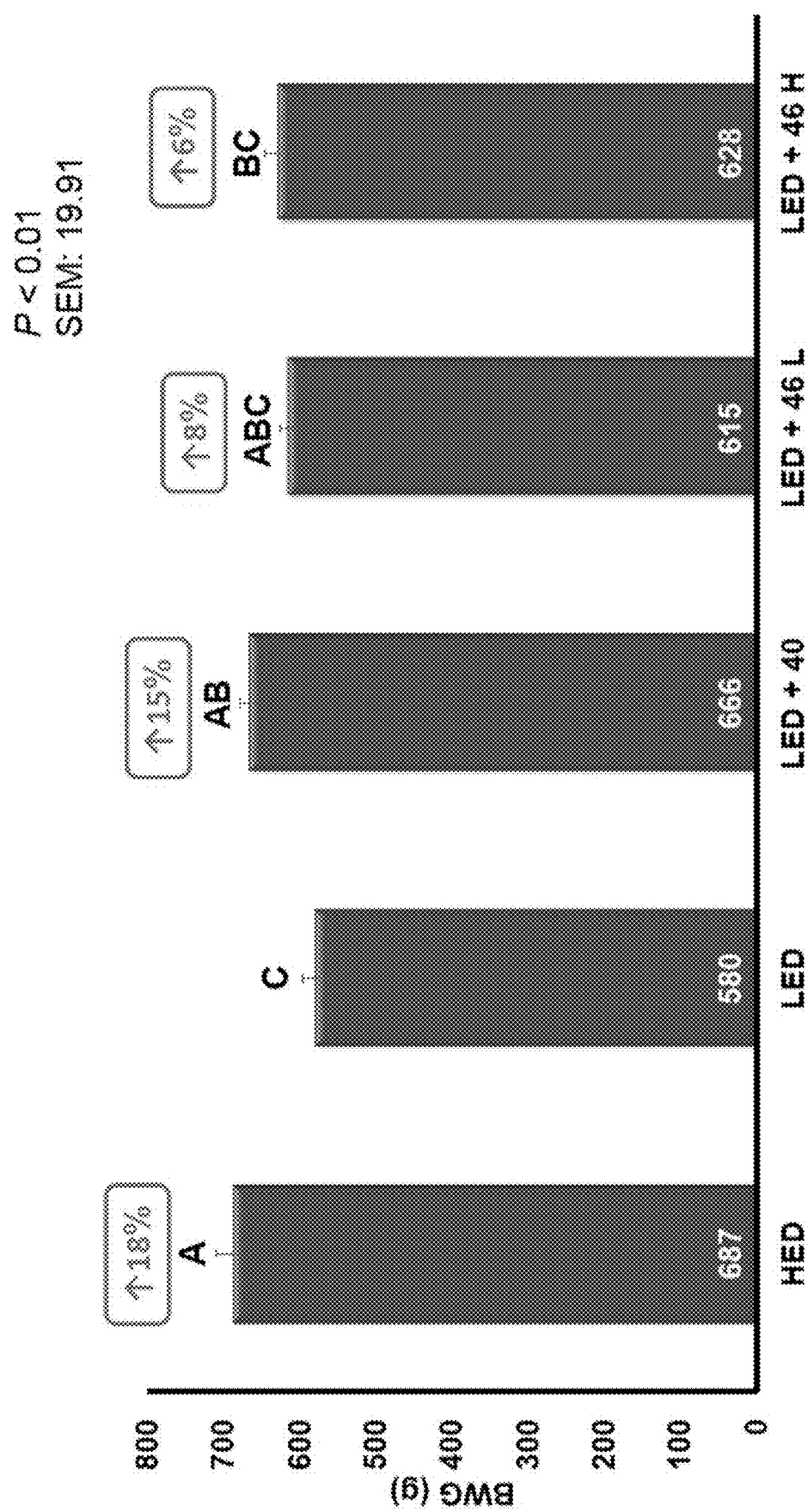
FIG. 12 shows body weight gain (D0-21) of broilers fed a low energy diet with or without dietary inclusion of a *Bacillus* direct fed microbial.

In FIG. 12, the body weight gain of birds fed a low energy diet supplemented with a *Bacillus* direct fed microbial were compared to birds fed low (LED) or high energy diets (HED). Isolates used in this experiment consisted of isolate 40 and a low (46L) and high (46H) dose of isolate 46. Those doses were used to confirm there would be no detrimental effects if spores were added at a lower or higher dose than recommended. Birds in the LED+40 and HED groups had increased body weight gain from D0-21 when compared to those fed LED without *Bacillus* supplementation. The LED+46H treatment numerically increased body weight compared to LED and was not statistically different from birds fed HED The overall ANOVA P-value is shown with letters above bars denoting significant differences among groups according to a Tukey's honest significance difference (HSD) test.

Figure 13:
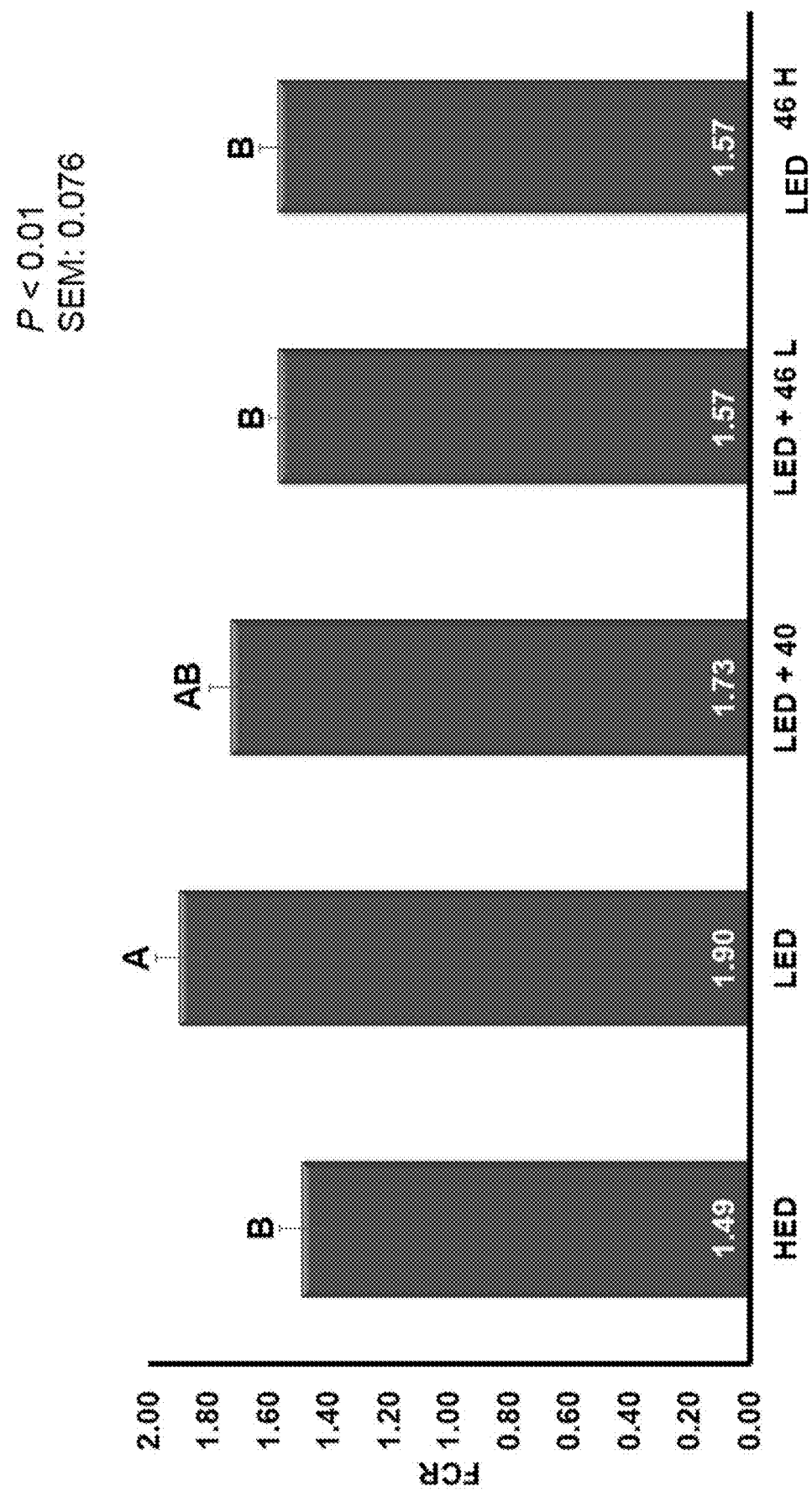
FIG. 13 shows feed conversion ratio (D0-21) of broilers fed a low energy diet with or without dietary inclusion of a *Bacillus* direct fed microbial.

In FIG. 13, the feed conversion ratio of birds fed a low energy diet supplemented with a *Bacillus* direct fed microbial were compared to birds fed low (LED) or high energy diets (HED). Isolates used in this experiment consisted of isolate 40 and low (46L) and high (46H) dose of isolate 46. The LED group had increased FCR when compared to the birds fed HED The LED+40 group was intermediate between the HED and LED groups, while both doses of isolate 46 significantly reduced FCR compared to LED and were not statistically different from the HED group. The overall ANOVA P-value is shown with letters above bars denoting significant differences among groups according to a Tukey's honest significance difference (HSD) test.

Figure 14:
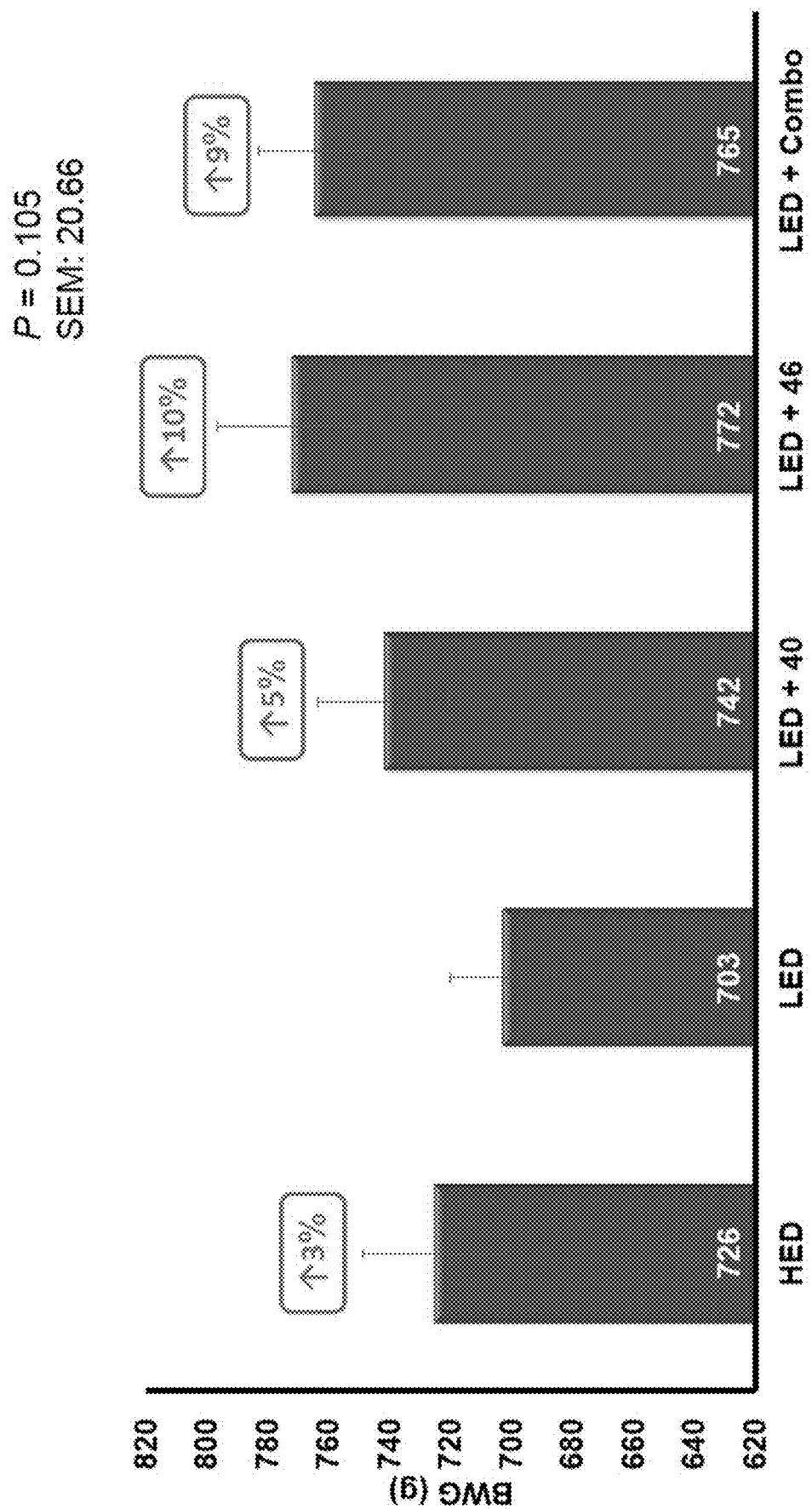
FIG. 14 shows body weight gain (D0-21) of broilers fed a low energy diet with or without dietary inclusion of a *Bacillus* direct fed microbial.

In FIG. 14, the body weight gain of birds fed a low energy diet supplemented with a *Bacillus* direct fed microbial were compared to birds fed low (LED) or high energy diets (HED). Isolates used in this experiment consisted of isolates 40, 46, and the combination of the two. In this experiment there were no statistical differences across all groups, though inclusion of isolate 40, 46, and the combination tended to increase body weight gain compared to the LED and HED. The overall ANOVA P-value is shown.

Figure 15:
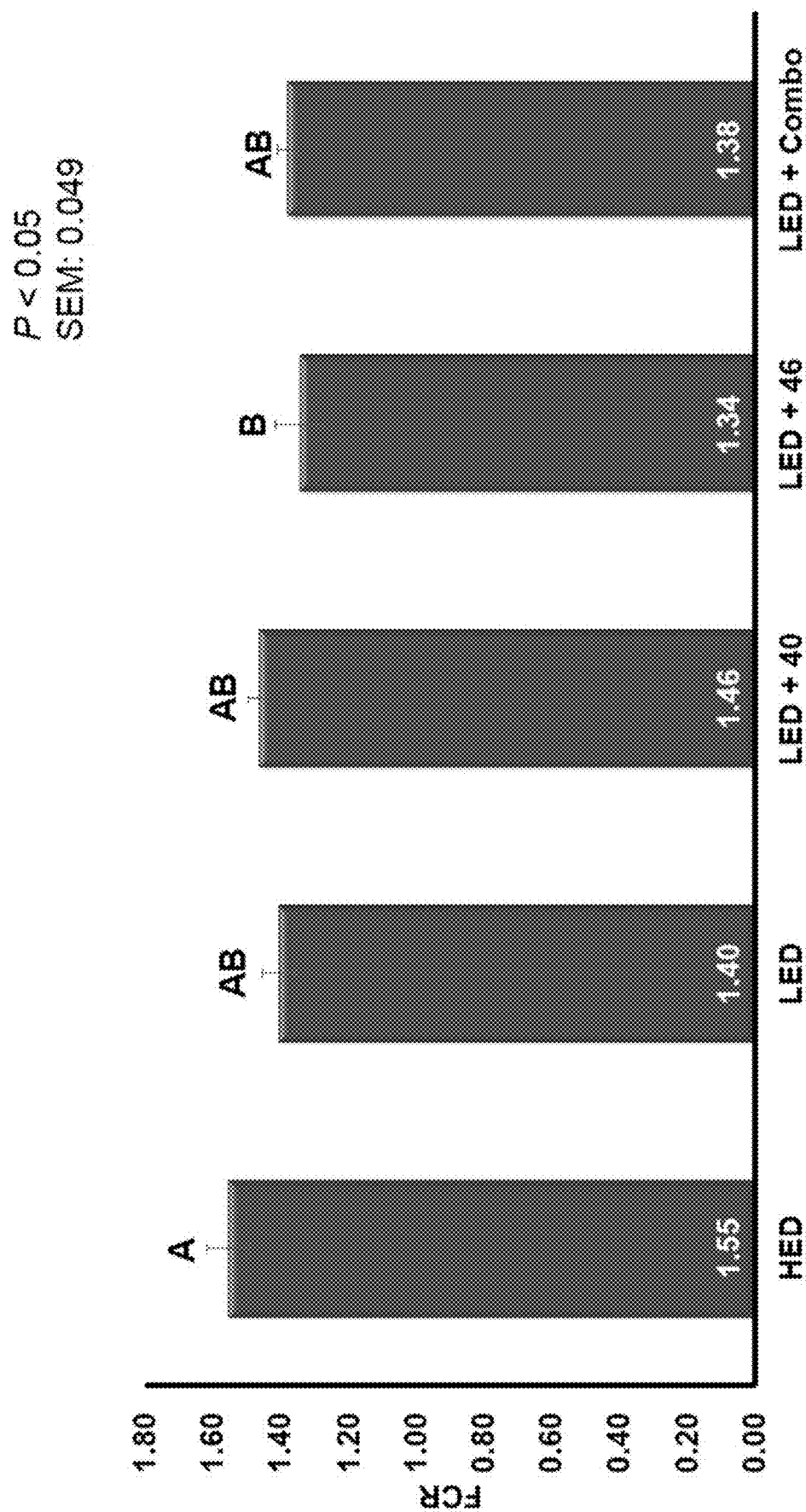
FIG. 15 shows feed conversion ratio (D0-21) of broilers fed a low energy diet with or without dietary inclusion of a *Bacillus* direct fed microbial.

In FIG. 15, the feed conversion ratio of birds fed a low energy diet supplemented with a *Bacillus* direct fed microbial were compared to birds fed low (LED) or high energy diets (HED). Isolates used in this experiment consisted of isolates 40, 46, and the combination of the two. Birds fed the HED had increased FCR compared to birds fed the LED. There was a significant reduction in FCR in birds fed the LED+46 compared to birds fed the HED. The overall ANOVA P-value is shown with letters above bars denoting significant differences among groups according to a Tukey's honest significance difference (HSD) test.

Figure 16:
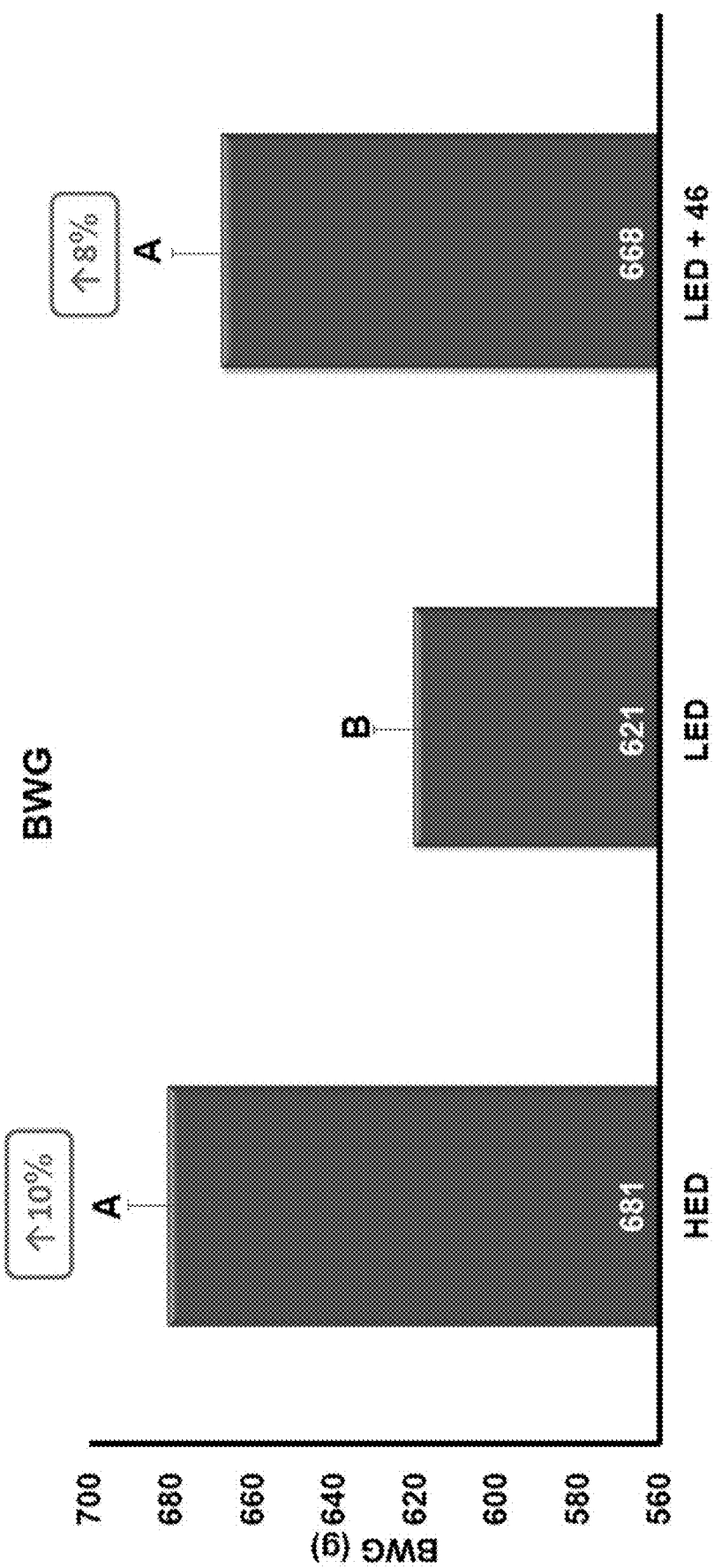
FIG. 16 shows body weight gain (D0-21) of pooled data from the previous 6 trials that included isolate 46.

In FIG. 16, data were pooled from the previous six experiments to further evaluate the responses across all trials in which isolate 46 was used due to the consistent positive responses to this isolate. Across all trials, birds fed the LED had a reduction in body weight gain of 10% compared to birds fed the HED, but birds fed the LED+46 were not statistically different from the birds fed the HED. The overall ANOVA P-value is shown with letters above bars denoting significant differences among groups according to a Tukey's honest significance difference (HSD) test.

Figure 17:
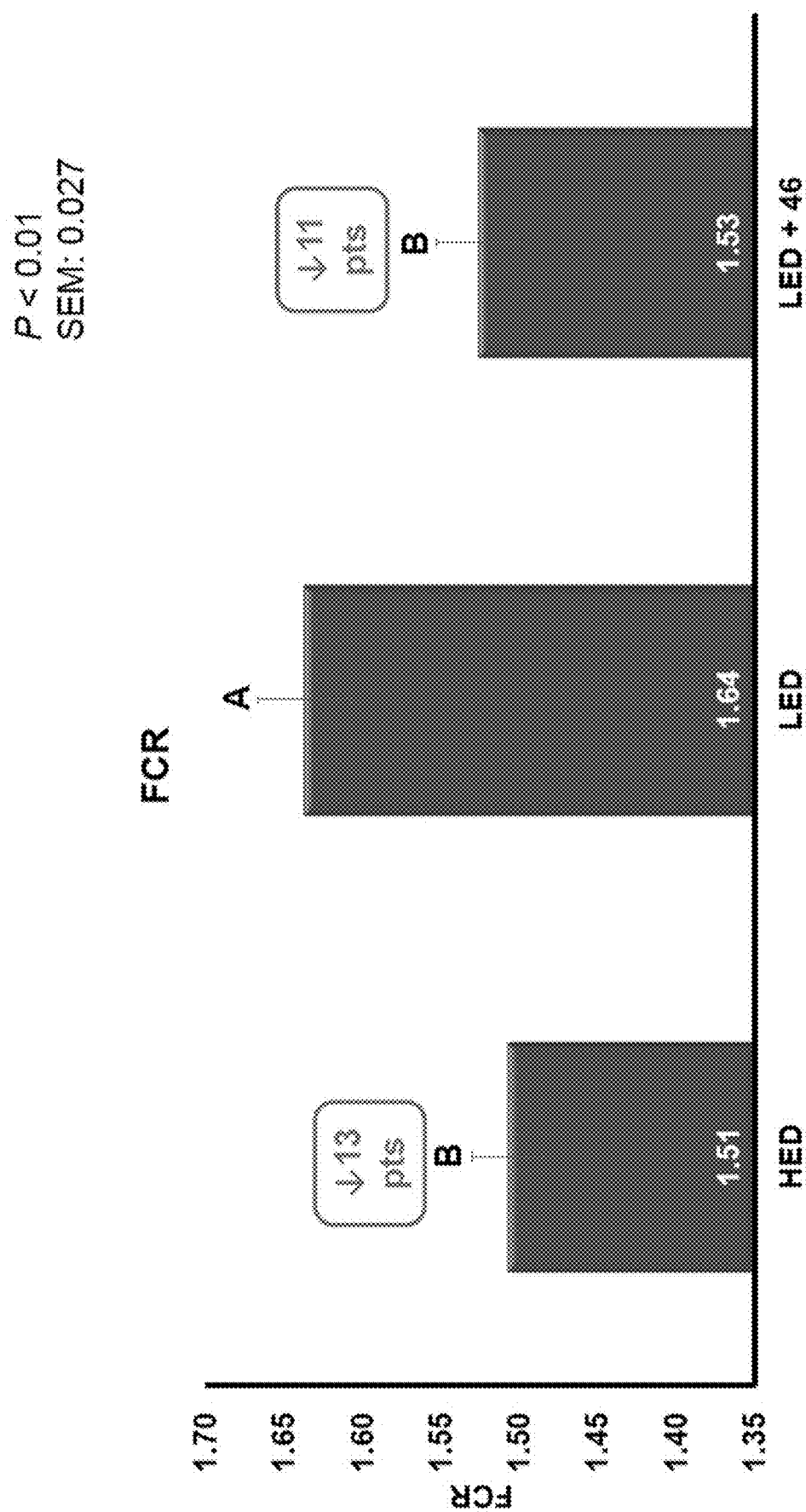
FIG. 17 shows feed conversion ratio (D0-21) of pooled data from the previous 6 trials that included isolate 46.

In FIG. 17, data were pooled from the previous six experiments to further evaluate the responses across all trials in which isolate 46 was used due to the consistent positive responses to this isolate. Across all trials, FCR was significantly increased by 13 points for birds fed LED compared to those fed HED The LED+46 group had a lower FCR than the LED group and was not statistically different from the HED group. The overall ANOVA P-value is shown with letters above bars denoting significant differences among groups according to a Tukey's honest significance difference (HSD) test. Thus isolate 46 seems to counteract the effect of feeding a LED.

In the following experiment, birds were reared in floor pens from 0-35 d poast-hatch and fed starter (0-14 d), grower (15-28 d), and finisher (29-35 d) diets. A control diet was formulated to industry relevant nutrient specifications and based on corn soybean meal (HED), whereas a low energy diet (LED) was formulated to be similar, except for 125 kcal/kg reduction in dietary energy (Table 6). All experimental diets were fed as both mash and crumble or pelleted diets to confirm efficacy of *Bacillus* isolates in pelleted diets. *Bacillus* isolates were added to the feed premix prior to the mixing of the individual treatments to ensure proper distribution of the spores throughout the feed. Spores were added to the feed at a quantity that would ensure a final spore count of approximately $10^6$ in the finished feed. Birds were provided feed ad libitum for the duration of the trial with the spores provided in their respective treatment throughout all feeding phases. Growth performance parameters were measured at the end of each feeding phase on days 14, 28, and 35. Birds were processed on D36 to determine foot pad dermatitis lesions and carcass characteristics.

TABLE 6

Ingredient and calculated nutrient composition (% as-fed) of starter, grower, and finisher diets (high energy diet (HED) and low energy diet (LED)), supplemented without or with *Bacillus* isolates from 0 to 35 d Post-hatch.

| | Starter | | Grower | | Finisher | |
| --- | --- | --- | --- | --- | --- | --- |
| Item | HED | LED | HED | LED | HED | LED |
| Ingredients (%) | | | | | | |
| Corn | 54.19 | 57.07 | 62.19 | 65.08 | 64.87 | 67.76 |
| Soybean Meal | 38.91 | 38.45 | 31.14 | 30.68 | 28.27 | 27.81 |
| Soy Oil | 3.19 | 0.77 | 2.94 | 0.51 | 3.53 | 1.11 |
| Dicalcium-Phosphate | 1.63 | 1.62 | 1.51 | 1.50 | 1.31 | 1.29 |
| Limestone | 0.91 | 0.92 | 0.90 | 0.91 | 0.84 | 0.86 |
| DL-methionine | 0.26 | 0.26 | 0.28 | 0.28 | 0.25 | 0.25 |
| L-lysine HCL | 0.03 | 0.04 | 0.15 | 0.16 | 0.12 | 0.12 |
| L-threonine | 0.07 | 0.07 | 0.08 | 0.08 | 0.06 | 0.06 |
| NB 3000 | 0.25 | 0.25 | 0.25 | 0.25 | 0.25 | 0.25 |

TABLE 6-continued

Ingredient and calculated nutrient composition (% as-fed) of starter, grower, and finisher diets (high energy diet (HED) and low energy diet (LED)), supplemented without or with *Bacillus* isolates from 0 to 35 d Post-hatch.

| | Starter | | Grower | | Finisher | |
|---|---|---|---|---|---|---|
| Item | HED | LED | HED | LED | HED | LED |
| Salt | 0.40 | 0.40 | 0.40 | 0.40 | 0.40 | 0.40 |
| Choline Chloride (60%) | 0.06 | 0.06 | 0.04 | 0.04 | 0.04 | 0.03 |
| BioCox 60 | 0.05 | 0.05 | 0.05 | 0.05 | — | — |
| Inert Filler[1] | 0.02 | 0.02 | 0.02 | 0.02 | 0.02 | 0.02 |
| Calculated analysis | | | | | | |
| $AME_n$, kcal/kg[2] | 3,025 | 2,900 | 3,095 | 2,970 | 3,165 | 3,040 |
| CP (%) | 23.00 | 23.00 | 20.00 | 20.00 | 18.75 | 18.75 |
| dLys (%)[3] | 1.22 | 1.22 | 1.12 | 1.12 | 1.02 | 1.02 |

[1] Spores were added at the expense of sand
[2] $AME_n$ = Nitrogen corrected apparent metabolizable energy
[3] dLys = Digestible lysine

TABLE 7

Live performance of broilers fed mash or pelleted high soybean meal control (HED) or low energy diets (LED), with or without *Bacillus*-based DFM supplementation, during starter (0-14 d) and grower (15-28 d) phases.[1]

| | Starter (0-14 d) | | | Grower (15-28 d) | | |
|---|---|---|---|---|---|---|
| Item[2] | BWG, kg | FI, kg | FCR | BWG, kg | FI, kg | FCR |
| Main effect of FF | | | | | | |
| Mash | $0.280^b$ | $0.411^b$ | $1.490^a$ | $1.010^b$ | $1.501^b$ | 1.493 |
| Crumble/Pellet | $0.404^a$ | $0.530^a$ | $1.320^b$ | $1.275^a$ | $1.894^a$ | 1.487 |
| SEM | 0.010 | 0.010 | 0.018 | 0.021 | 0.031 | 0.005 |
| Main effect of Diet | | | | | | |
| HED | 0.350 | 0.478 | $1 394^{ab}$ | 1.160 | 1.677 | $1.450^b$ |
| LED | 0.334 | 0.471 | $1.444^a$ | 1.129 | 1.704 | $1.507^a$ |
| LED + 46 | 0.344 | 0.460 | $1.361^b$ | 1.139 | 1.709 | $1.503^a$ |
| LED + combo | 0.339 | 0.472 | $1 421^{ab}$ | 1.141 | 1.699 | $1.501^a$ |
| SEM | 0.013 | 0.014 | 0.025 | 0.030 | 0.044 | 0.007 |
| P-Values[3] | | | | | | |
| FF | <0.0001 | <0.0001 | <0.0001 | <0.0001 | <0.0001 | 0.35 |
| Diet | 0.233 | 0.373 | 0.016 | 0.364 | 0.644 | <0.0001 |
| FF × Diet | 0.459 | 0.727 | 0.766 | 0.673 | 0.984 | 0.261 |

$^{ab}$Means within a column that do not share a common superscript are different (P < 0.05)
[1] Values are LSMeans of 24 replicate pens for FF and 12 replicate pens for Diet
[2] Abbreviations: DFM = direct fed microbial; LED = low energy diet with 125 kcal/kg reduction in apparent $ME_n$; LED + 46 = LED with *Bacillus* isolate 46; LED + Combo = LED with *Bacillus* isolates 40 + 46; FF = feed form
[3] Overall ANOVA P-values The body weight gain, feed intake, and feed conversion ratio of birds fed a low energy diet supplemented with a *Bacillus* direct fed microbial were compared to birds fed only a low energy diet (LED) or high energy diet (HED) during the starter and grower phases (Table 7). Isolates used in this experiment consisted of isolate 46 and combination of 40 and 46 (combo). There were no statistical differences in BWG or FI during the starter phase, however the LED+46 treatment numerically increased BWG compared to the LED and lowered FI compared to all other groups. Birds fed LED+46 had lower FCR than birds fed the LED and a similar FCR to birds fed the HED Similarly, in the grower phase, there was no statistical differences among groups in BWG or FI, but the birds fed LED+46 and LED+combo had numerically higher BWG compared to those fed the LED. Birds fed the HED had significantly lower FCR than all other groups.

TABLE 8

Live performance of broilers fed mash or pelleted high soybean meal control (HED) or low energy diets (LED), with or without *Bacillus*-based DFM candidates during finisher (29-35 d) and overall (0-35 d) phases.[1]

| Item[2] | Finisher (29-35 d) | | | Overall (0-35 d) | | |
|---|---|---|---|---|---|---|
| | BWG, kg | FI, kg | FCR | BWG, kg | FI, kg | FCR |
| Main effect of FF | | | | | | |
| Mash | 0.748 | 2.408[b] | 1.637[b] | 2.038[b] | 4.321[b] | 1.548[a] |
| Crumble/Pellet | 0.775 | 2.603[a] | 1.678[a] | 2.454[a] | 5.027[a] | 1.528[b] |
| SEM | 0.013 | 0.022 | 0.010 | 0.034 | 0.059 | 0.005 |
| Main effect of Diet | | | | | | |
| HED | 0.791 | 2.426[b] | 1.639 | 2.302 | 4.583 | 1.501[b] |
| LED | 0.770 | 2.542[a] | 1.664 | 2.234 | 4.719 | 1.554[a] |
| LED + 46 | 0.753 | 2.536[a] | 1.650 | 2.237 | 4.705 | 1.546[a] |
| LED + combo | 0.730 | 2.517[a] | 1.675 | 2.211 | 4.689 | 1.552[a] |
| SEM | 0.018 | 0.031 | 0.014 | 0.049 | 0.083 | 0.008 |
| P-Values[3] | | | | | | |
| FF | 0.156 | <0.0001 | 0.003 | <0.0001 | <0.0001 | 0.005 |
| Diet | 0.125 | 0.001 | 0.238 | 0.064 | 0.104 | <0.0001 |
| FF × Diet | 0.825 | 0.644 | 0.018[4] | 0.982 | 0.986 | 0.843 |

[a,b]Means within a column that do not share a common superscript are different (P < 0.05)
[1]Values are LSMeans of 24 replicate pens for FF and 12 replicate pens for Diet
[2]Abbreviations: DFM = direct fed microbial; LED = low energy diet with 125 kcal/kg reduction in apparent $ME_n$; LED + 46 = LED with *Bacillus* isolate 46; LED + Combo = LED with *Bacillus* isolates 40 + 46; FF = feed form
[3]Overall ANOVA P-values
[4]Interaction means of FF × Diet for Finisher FCR: Mash, HED = 1.586[b]; Mash, LED = 1.662[ab]; Mash, LED + 46 = 1.651[ab]; Mash, LED + combo = 1.650[ab]; Pellet, HED = 1.694[a]; Pellet, LED = 1.668[ab]; Pellet, LED + 46 = 1.649[ab]; Pellet, LED + combo = 1.702[a]

The body weight gain, feed intake, and feed conversion ratio of birds fed a low energy diet supplemented with a *Bacillus* direct fed microbial were compared to birds fed only a low energy diet (LED) or high energy diet (HED) during the finisher and overall phases (Table 8). Isolates used in this experiment consist of isolate 46 and combination of 40 and 46. There were no differences in body weight gain or FCR during the finisher phase, however birds fed HED had a lower feed intake (FI) than all other groups. For the overall period, there were no differences in BWG or FI, but birds fed HED had significantly lower FCR compared to other groups.

TABLE 9

Carcass characteristics of broilers fed high soybean meal (HED) or low energy diets (LED) supplemented without or with *Bacillus*-based DFM candidates from 0 to 35 d and processed at 36 d post-hatch.[1]

| Item[2] | Hot Carcass | | Hot Fat Pad | | Chilled Carcass | |
|---|---|---|---|---|---|---|
| | Weight, kg | Yield, % | Weight, kg | Yield, % | Weight, kg | Yield, % |
| HED | 1.808 | 73.03[b] | 0.027 | 1.15 | 1.833 | 74.07[b] |
| LED | 1.797 | 73.28[ab] | 0.028 | 1.19 | 1.820 | 74.24[ab] |
| LED + 46 | 1.825 | 73.86[a] | 0.029 | 1.19 | 1.854 | 75.04[a] |
| LED + combo | 1.803 | 73.65[ab] | 0.027 | 1.29 | 1.827 | 74.62[ab] |
| SEM | 0.015 | 0.22 | 0.0008 | 0.040 | 0.016 | 0.252 |
| P-value[3] | 0.630 | 0.033 | 0.517 | 0.116 | 0.540 | 0.030 |

[a,b]Means within a column that do not share a common superscript are different (P < 0.05)
[1]Values are LSMeans of 8 replicate pens
[2]Abbreviations: DFM = direct fed microbial; LED = low energy diet with 125 kcal/kg reduction in apparent $ME_n$; LED + 46 = LED with *Bacillus* isolate 46; LED + Combo = LED with *Bacillus* isolates 40 + 46
[3]Overall ANOVA P-values On day 36, 8 pens per group of only the birds fed pelleted diets were randomly selected for processing and carcass characteristics were compared across groups (Table 9). Birds fed the LED+46 had numerically higher hot carcass weights than all other groups. This group also had a significantly higher hot carcass yield percentage compared to the HED group. There was no difference in hot fat pad weight or yield among groups. Similarly, the LED+46 treatment numerically increased chilled carcass weights of birds over all other groups and increased yield when compared to the HED group.

TABLE 10

Parts weights and yields of broilers fed high soybean meal (HED) or low energy diets (LED) supplemented without or with *Bacillus*-based DFM candidates from 0 to 35 d and processed at 36 d post-hatch.[1]

| Item[2] | Breast | | Tenders | | Total White Meat | |
|---|---|---|---|---|---|---|
| | Weight, kg | Yield, % | Weight, kg | Yield, % | Weight, kg | Yield, % |
| HED | 0.473 | 19.11$^{ab}$ | 0.093 | 3.74$^b$ | 0.566 | 22.86$^{ab}$ |
| LED | 0.464 | 18.90$^b$ | 0.093 | 3.80$^{ab}$ | 0.557 | 22.65$^b$ |
| LED + 46 | 0.484 | 19.56$^a$ | 0.096 | 3.92$^a$ | 0.581 | 23.48$^a$ |
| LED + combo | 0.473 | 19.28$^{ab}$ | 0.094 | 3.84$^{ab}$ | 0.567 | 23.13$^{ab}$ |
| SEM | 0.006 | 0.16 | 0.001 | 0.041 | 0.006 | 0.19 |
| P-value[3] | 0.132 | 0.020 | 0.162 | 0.014 | 0.125 | 0.007 |

$^{ab}$Means within a column that do not share a common superscript are different (P < 0.05)
[1]Values are LSMeans of 8 replicate pens
[2]Abbreviations: DFM = direct fed microbial; LED = low energy diet with 125 kcal/kg reduction in apparent ME$_n$; LED + 46 = LED with *Bacillus* isolate 46; LED + Combo = LED with *Bacillus* isolates 40 + 46
[3]Overall ANOVA P-values Weight and yield were also compared across parts (i.e., breast, tenders, and total white meat; Table 10). The breast yield percentage for LED+46 was significantly higher than that of the LED group. The same effect was observed for tender yield as LED+46 which was significantly increased in the LED+46 group compared to the HED group. Correspondingly, total white meat weight was numerically increased in the LED+46 group compared to all other groups and the yield percentage for the LED+46 group was significantly higher than that of the LED group.

TABLE 11

Percentage distribution of footpad dermatitis scores of broilers fed high soybean meal (HED) or low energy diets (LED) supplemented without or with *Bacillus*-based DFM candidates from 0 to 35 d.[1]

| Item[2] | 0 | 1 | 2 |
|---|---|---|---|
| HED | 11.65$^b$ | 83.14$^a$ | 5.21 |
| LED | 10.21$^b$ | 78.24$^a$ | 11.55 |
| LED + 46 | 34.47$^a$ | 59.00$^b$ | 6.53 |
| LED + combo | 33.52$^a$ | 57.95$^b$ | 8.52 |
| SEM | 5.88 | 5.44 | 3.21 |
| P-value[3] | 0.0002 | 0.0002 | 0.625 |

$^{ab}$Means within a column that do not share a common superscript from arc sine transformed data are different (P < 0.05)
[1]Values are LSMeans of 8 replicate pens
[2]Abbreviations: DFM = direct fed microbial; LED = low energy diet with 125 kcal/kg reduction in apparent ME$_n$; LED + 46 = LED with *Bacillus* isolate 46; LED + Combo = LED with *Bacillus* isolates 40 + 46
[3]Overall ANOVA P-values from arc sine transformed data Footpad dermatitis was subjectively scored across the treatment groups on a scale from 0-2, in which a score of 0 indicates no lesions or very small superficial lesions, a score of 1 indicates mild lesions and discoloration of the footpad, and a score of 2 indicates severe lesions with ulcers or scabs and swollen foot pads. There was a significant increase in the proportion of "0" scores for the LED+46 and LED+combo groups compared to the HED and LED groups (Table 11). Additionally, there was a significant reduction in scores of "1" in the LED+46 and LED+combo groups compared to HED and LED groups. There were no differences observed in scores of "2" among all groups.

In conclusion, feeding isolate 46 in a low energy diet provided similar performance to higher energy, more expensive diet, and also improved carcass characteristics and lowered the incidence of footpad pododermatitis lesions.

DEPOSIT INFORMATION

A deposit of the *Bacillus amyloliquefaciens* isolate designated as "Isolate 46" disclosed above and recited in the appended claims has been made with the ARS Culture Collection (NRRL), 1815 N. University Street, Peoria, IL 61604. The date of deposit was Jun. 12, 2020. All restrictions will be irrevocably removed upon granting of a patent, and the deposit is intended to meet all of the requirements of 37 C.F.R. §§ 1.801-1.809. The NRRL Accession Number is B-67957. The deposit will be maintained in the depository for a period of thirty years, or five years after the last request, or for the enforceable life of the patent, whichever is longer, and will be replaced as necessary during that period.

A deposit of the *Bacillus amyloliquefaciens* isolate designated as "Isolate 40" disclosed above and recited in the appended claims has been made with the ARS Culture Collection (NRRL), 1815 N. University Street, Peoria, IL 61604. The date of deposit was Jun. 12, 2020. All restrictions will be irrevocably removed upon granting of a patent, and the deposit is intended to meet all of the requirements of 37 C.F.R. §§ 1.801-1.809. The NRRL Accession Number is B-67956. The deposit will be maintained in the depository for a period of thirty years, or five years after the last request, or for the enforceable life of the patent, whichever is longer, and will be replaced as necessary during that period.

We claim:

1. A poultry feed composition comprising a plant-based food source and at least one *Bacillus* isolate selected from: (a) a *Bacillus* isolate designated as "Isolate 46" and deposited at the Agricultural Research Service Culture Collection (NRRL) under accession number B-67957, and (b) a *Bacillus* isolate designated as "Isolate 40" and deposited at the NRRL under accession number B-67956; wherein the poultry feed composition comprises between about $10^4$-$10^{12}$ spores of the *Bacillus* isolate per gram of total poultry feed composition.

2. The poultry feed composition of claim 1, wherein the plant-based food source comprises an anti-nutritional factor.

3. The poultry feed composition of claim 2, wherein the anti-nutritional factor is selected from the group consisting of galactosides, raffinose, stachyose, cellulose, galactomannan, xylan, xylose, phytate, lectins, trypsin inhibitors, and other enzyme-inhibiting or antigenic proteins (e.g., β-conglycinin).

4. The poultry feed composition of claim 1, wherein the plant-based food source is or is derived from soybean, fermented soybean meal, rapeseed/canola, sunflower, palm kernel, copra, linseed, peanut, sesame seed, other oilseeds, or cereal grains such as corn, wheat, sorghum, barley, rye, triticale, or oats.

5. The poultry feed composition of claim 1, wherein the poultry feed composition is a low energy diet (LED) feed composition that has 1-10% lower energy content as compared to a standard poultry diet as measured in kcal/kg$^2$.

6. The poultry feed composition of claim 1, wherein the composition comprises both of the *Bacillus* isolates.

7. A method for improving nutritional uptake in a subject comprising administering to the subject the poultry feed composition of claim 1, wherein the subject is a poultry species.

8. The method of claim 7, wherein the improved nutritional uptake is demonstrated by improved body weight gain, an improved cumulative feed conversion ratio, or improved carcass characteristics.

9. A method for producing the poultry feed composition of claim 1 comprising introducing the at least one *Bacillus* isolate into a plant-based food source.

10. The method of claim 9, further comprising pelleting the animal poultry feed composition.

11. The method of claim 10, wherein the at least one *Bacillus* isolate is introduced into the plant-based food source prior to the pelleting of the poultry feed composition.

12. The method of claim 9, wherein the plant-based food source comprises an anti-nutritional factor.

13. The method of claim 9, wherein the poultry feed composition is a low energy diet (LED) feed composition.

14. The method of claim 9, wherein the plant-based food source is fermented with the *Bacillus* isolate prior to packaging.

15. A method for reducing the incidence of footpad dermatitis in poultry, the method comprising administering to the poultry an effective amount of the poultry feed composition of claim 1.

* * * * *